United States Patent
Kruck et al.

(10) Patent No.: US 12,246,197 B2
(45) Date of Patent: Mar. 11, 2025

(54) AGENT FOR DYEING KERATINOUS MATERIAL, IN PARTICULAR HUMAN HAIR, COMPRISING AMINOSILICONES, PIGMENTS AND ALKYLPOLYGLYCOSIDES

(71) Applicant: Henkel AG & Co. KGaA, Duesseldorf (DE)

(72) Inventors: Constanze Kruck, Grevenbroich (DE); Sandra Hilbig, Bochum (DE); Melanie Moch, Dormagen (DE); Daniela Kessler-Becker, Leverkusen (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 0 days.

(21) Appl. No.: 18/002,466

(22) PCT Filed: Jun. 7, 2021

(86) PCT No.: PCT/EP2021/065138
§ 371 (c)(1),
(2) Date: Dec. 19, 2022

(87) PCT Pub. No.: WO2021/254804
PCT Pub. Date: Dec. 23, 2021

(65) Prior Publication Data
US 2023/0233881 A1    Jul. 27, 2023

(30) Foreign Application Priority Data

Jun. 19, 2020 (DE) .......................... 102020207602.2

(51) Int. Cl.
*A61Q 5/10* (2006.01)
*A61K 8/60* (2006.01)
*A61K 8/898* (2006.01)
*A61Q 5/06* (2006.01)

(52) U.S. Cl.
CPC .............. *A61Q 5/065* (2013.01); *A61K 8/604* (2013.01); *A61K 8/898* (2013.01)

(58) Field of Classification Search
CPC ......... A61Q 5/065; A61K 8/604; A61K 8/898
USPC ............................................................. 8/405
See application file for complete search history.

(56) References Cited

U.S. PATENT DOCUMENTS

| | | | | |
|---|---|---|---|---|
| 8,845,759 B2 * | 9/2014 | Neuba | ..................... | A61K 8/498 8/405 |
| 2010/0083446 A1 * | 4/2010 | Brun | ..................... | A61K 8/891 8/405 |

FOREIGN PATENT DOCUMENTS

| | | | | |
|---|---|---|---|---|
| WO | 0232383 A2 | 4/2002 | | |
| WO | 2014037159 A2 | 3/2014 | | |
| WO | 2014180980 A1 | 11/2014 | | |
| WO | WO 2017108828 A1 * | 6/2017 | ............. | A61K 8/411 |

OTHER PUBLICATIONS

STIC Search Report dated Apr. 1, 2024.*
Mintel, Scwarzkopf & Henkel, Permanent Hair Colour, ID#5900909, Mintel GNPD [online], Aug. 2018, Internet URL : https://portal.mintel.com.

* cited by examiner

*Primary Examiner* — Eisa B Elhilo
(74) *Attorney, Agent, or Firm* — Lorenz & Kopf, LLP

(57) ABSTRACT

An agent for dying (e.g. coloring) keratinous material, in particular human hair, is disclosed. The agent comprises (a1) at least one alkyl (poly)glycoside, (a2) at least one pigment, and (a3) at least one amino-functionalized silicone polymer. A process for dyeing keratinous material with the agent is also disclosed. The process comprises preparing an application mixture comprising, applying the application mixture to keratinous material for a time sufficient to expose the keratinous material to the agent, and then rinsing the application mixture from the keratinous material with water. A multicomponent packaging unit (kit-of-parts) for dyeing keratinous material with the agent is also disclosed.

20 Claims, No Drawings

AGENT FOR DYEING KERATINOUS MATERIAL, IN PARTICULAR HUMAN HAIR, COMPRISING AMINOSILICONES, PIGMENTS AND ALKYLPOLYGLYCOSIDES

CROSS-REFERENCE TO RELATED APPLICATION

This application is a U.S. National-Stage entry under 35 U.S.C. § 371 based on International Application No. PCT/EP2021/065138, filed Jun. 7, 2021, which was published under PCT Article 21(2) and which claims priority to German Application No. 102020207602.2, filed Jun. 19, 2020, which are all hereby incorporated in their entirety by reference.

TECHNICAL FIELD

The subject of the present application is an agent for coloring keratinous material, in particular human hair, which comprises at least one alkyl (poly)glycoside (a1), at least one pigment (a2) and at least one amino-functionalized silicone polymer (a3).

Further objects of this application are processes for dyeing keratinous material, in particular human hair, wherein a ready-to-use dyeing agent is first prepared by mixing various agents, said agents comprising alkyl (poly)glycoside (a1), pigment (a2) and amino-functionalized silicone polymer (a3). These ready-to-use agents are applied to the keratin fibers, left to act, and rinsed out again.

BACKGROUND

Further objects of this application are multi-component packaging units which, separately packaged in different containers, comprise the agents (I), (II) and optionally (III), these agents comprising alkyl (poly)glycoside (a1), pigment (a2) and amino-functionalized silicone polymer (a3).

Changing the shape and color of keratinous material, especially human hair, is a key area of modern cosmetics. To change the hair color, the expert knows various coloring systems depending on the coloring requirements. Oxidation dyes are usually used for permanent, intensive dyeing with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing obtained with direct dyes have a shorter shelf life and quicker wash ability. Dyes with direct colorings usually remain on the hair for a period of between 5 and 20 washes.

The use of color pigments is known for short-term color changes on the hair and/or skin. Color pigments are understood to be insoluble, coloring substances. These are present undissolved in the dye formulation in the form of small particles and are only deposited from the outside on the hair fibers and/or the skin surface. Therefore, they can usually be removed again without residue by a few washes with detergents comprising surfactants. Various products of this type are available on the market under the name hair mascara.

If the user wants particularly long-lasting dyeing, the use of oxidative dyes has so far been his/her only option. However, despite numerous optimization attempts, an unpleasant ammonia or amine odor cannot be completely avoided in oxidative hair dyeing. The hair damage still associated with the use of oxidative dyes also has a negative effect on the user's hair. A challenge that still exists is therefore the search for alternative, high-performance dyes, and dyeing processes. Recently, particular focus has been placed on pigment-based dyeing systems.

It was the task of the present disclosure to provide a coloring agent that enables pigments to be fixed to the hair in an extremely durable manner. When the agent is used in a dyeing process, particularly intensive dyeing results should be achieved with good fastness to washing, good leveling capacity and a particularly uniform color result.

BRIEF SUMMARY

An agent for dyeing keratinous material is provided. The agent comprises (a1) at least one alkyl (poly)glycoside, (a2) at least one pigment, and (a3) at least one amino-functionalized silicone polymer.

A process for dyeing keratinous material (e.g. human hair) with the agent is also provided. The process comprises:
applying the agent to keratinous fibers; and
optionally, rinsing the keratinous fibers to remove the agent after an exposure time of from about 30 seconds to about 45 minutes.

In embodiments, the process comprises:
preparing an application mixture comprising the agent by mixing together
  (I) a first agent comprising the at least one alkyl(poly)glycoside (a1) and the at least pigment (a2), and
  (II) a second agent comprising the at least one amino-functionalized silicone polymer (a3);
applying the application mixture to keratinous material for a time sufficient to expose the keratinous material to the agent; and
rinsing the application mixture from the keratinous material with water.

In embodiments, the process comprises:
preparing an application mixture comprising the agent by mixing together
  (I) a first agent comprising the at least one alkyl(poly)glycoside (a1),
  (II) a second agent comprising the at least pigment (a2), and
  (III) a third agent comprising the at least one amino-functionalized silicone polymer (a3);
applying the application mixture to keratinous material for a time sufficient to expose the keratinous material to the agent; and
rinsing the application mixture from the keratinous material with water.

A multicomponent packaging unit (kit-of-parts) for dyeing keratinous material with the agent is also provided. The multicomponent packaging unit comprises, in some embodiments, separately packaged:
a first container comprising (I) a first agent comprising the at least one alkyl(poly)glycoside (a1) and the at least pigment (a2); and
a second container comprising (II) a second agent comprising the at least one amino-functionalized silicone polymer (a3).

In some embodiments, multicomponent packaging unit (kit-of-parts) for dyeing keratinous material comprises, separately packaged:

a first container comprising (I) a first agent comprising the at least one alkyl(poly)glycoside (a1);

a second container comprising (II) a second agent comprising the at least pigment (a2); and a third container comprising (III) a third agent comprising the at least one amino-functionalized silicone polymer (a3).

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description. It is to be appreciated that all numerical values as provided herein, save for the actual examples, are approximate values with endpoints or particular values intended to be read as "about" or "approximately" the value as recited.

Surprisingly, it has now been found that the task can be excellently solved if keratinous fibers, in particular hair, are dyed with an agent comprising at least one alkyl (poly)glycoside (a1), at least one pigment (a2) and at least one amino-functionalized silicone polymer (a3).

A first object of the present disclosure is an agent for coloring keratinous material, in particular human hair, comprising.

(a1) at least one alkyl (poly)glycoside,
(a2) at least one pigment, and
(a3) at least one amino-functionalized silicone polymer.

In the course of the work leading to the present disclosure, it was found that particularly good color results could be obtained when the pigment or pigments were applied to the keratin material, in particular human hair, in admixture with at least one alkyl(poly)glycoside and at least one amino silicone. In particular, the wash fastness of dyed hair was improved. In addition, the dyeing was also exemplified by a particularly high uniformity.

Keratinous Material

Keratinous material includes hair, skin, nails (such as fingernails and/or toenails). Wool, furs, and feathers also fall under the definition of keratinous material.

Preferably, keratinous material is understood to be human hair, human skin, and human nails, especially fingernails and toenails. Keratinous material is understood to be human hair.

Coloring Agent

The term "coloring agent" is used in the context of this present disclosure for a coloring of the keratin material, in particular the hair, caused using pigments. In this coloring process, the pigments are deposited as coloring compounds in a particularly homogeneous and uniform film on the surface of the keratin material.

As contemplated herein, the coloring agent represents an agent ready for use. This ready-to-use agent can, for example, be filled into a container and applied to the keratin material in this form without further dilution, mixing or other process steps. For reasons of storage stability, however, it has been found to be particularly preferable if the cosmetic agent ready for use is prepared by the hairdresser or user only shortly before application. For the preparation of the ready-to-use agent, for example, the mixture or predispersion of alkyl (poly)glycoside (a1) and pigment (a2) may be conducted with one or more further agents, one of these further agents being at least comprises an amino-functionalized silicone polymer (a3). However, it is equally conceivable that the ready-to-use agent is prepared by mixing at least three different agents, one of these agents comprising at least one alkyl (poly)glycoside (a1), another agent comprising at least one pigment (a2) and still another agent comprising at least amino-functionalized silicone polymer (a3). The agents can be mixed, for example, by shaking, thus ensuring a particularly uniform distribution of the dispersed pigments.

In other words, a first subject matter of the present application is an agent for coloring keratinous material, in particular human hair, comprising in a cosmetic carrier (a1) at least one alkyl (poly)glycoside,
(a2) at least one pigment, and
(a3) at least one amino-functionalized silicone polymer.

Alkyl(poly)glycosides (a1)

As the first ingredient (a1) essential to the present disclosure, the agent comprises at least one alkyl (poly)glycoside. It was observed that the alkyl(poly)glycoside(s) on the one hand cause a particularly good and fine dispersion of the pigments in the agent. This fine-particle dispersion leads to a particularly uniform color result. On the other hand, it was also found that the combination of alkyl(poly)glycosides (a1) with pigment (a2) and amino silicone (a3) leads to dyeing with particularly good wash fastness.

Alkyl(poly)glycosides (APGs) are non-ionic surfactants produced entirely from renewable raw materials (sugar building blocks, glucose, e.g., from corn starch, and fatty alcohol, e.g., from coconut oil). Alkyl polyglycosides are accessible by acid catalyzed reaction (Fischer reaction) of sugars, especially glucose (or starch) or of butyl glycosides with fatty alcohols.

Complex mixtures of alkyl monoglucoside (alkyl-α-d- and -β-d-glucopyranoside as well as insignificant amounts of -glucofuranoside), alkyldiglucosides (-isomaltosides, -maltosides etc.) and alkyloligoglucosides (-maltotriosides, -tetraosides etc.) are formed. The average degree of polymerization of commercial products whose alkyl radicals are in the C8-C16 range is 1.2-1.5.

An alkyl monoglycoside obtained by reacting one molecule of a sugar component with one molecule of fatty alcohol may alternatively be referred to as an alkyl glycoside. If the proportion of sugar building blocks is higher than one, they are alkyl polyglycosides in the sense of the present disclosure. The term alkly(poly)glycoside in parentheses thus refers to a mixture of alkyl monoglycosides and the corresponding oligomeric or higher polymeric compounds, the alkylpolglycosides.

In other words, a first object of the present disclosure is an agent for coloring keratinous material, in particular human hair, comprising.

(a1) at least one alkyl polyglycoside,
(a2) at least one pigment, and
(a3) at least one amino-functionalized silicone polymer.

Particularly suitable for solving the problem as contemplated herein are the alkyl(poly)glycosides of the formula (APG-1)

where

Z is a sugar component from the group comprising glucose, fructose, galactose, arabinose, ribose, xylose, lyxose, allose, altrose, mannose, gulose, idose, talose and sucrose, x is a number from 1 to 10, preferably a number from 1 to 5, and n is a number from 7 to 29, preferably a number from 7 to 21, further preferably a number from 11 to 21, and most preferably a number from 11 to 17.

The radical Z stands for a sugar component selected from the group of glucose, fructose, galactose, arabinose, ribose, xylose, lyxose, allose, altrose, mannose, gulose, idose, talose and sucrose.

In the formula (APG-1) there is several sugar building blocks, the number of which corresponds to the value x. When the index number x takes a value greater than 1, there are multiple sugar building blocks in the formula (APG-1). In principle, different sugar components can also be included in each formula (APG-1) (in the case of x=2, for example, Z can stand for glucose and for fructose). Thus, any monosaccharides or oligosaccharides can be used as sugar building block Z. Usually sugars with 5 or 6 carbon atoms and the corresponding oligosaccharides are used. Such sugars include glucose, fructose, galactose, arabinose, ribose, xylose, lyxose, allose, altrose, mannose, gulose, idose, talose and sucrose.

The index number x represents a number from 1 to 10, preferably a number from 1 to 5. The index number n characterizes the length of the alkyl chain of the alkyl(poly)glycoside. n stands for a number from 7 to 29, preferably for a number from 7 to 21, further preferably for a number from 11 to 21 and most preferably for a number from 11 to 17. The total length of the alkyl chain is n+1.

Accordingly, in the context of a further embodiment, a particularly preferred agent is wherein it is (a1) comprises at least one alkyl (poly)glycoside of the formula (APG-1),

$(Z)_x$—O—$(CH_2)_n$—$CH_3$ (APG-1)

where

Z is a sugar component from the group comprising glucose, fructose, galactose, arabinose, ribose, xylose, lyxose, allose, altrose, mannose, gulose, idose, talose and sucrose, x is a number from 1 to 10, preferably a number from 1 to 5, and n is a number from 7 to 29, preferably a number from 7 to 21, further preferably a number from 11 to 21, and most preferably a number from 11 to 17.

As contemplated herein, alkyl polyglycosides corresponding to the general formula RO—$(Z)_x$, where R is alkyl, Z is sugar and x are the number of sugar units. Particularly preferred are those alkyl polyglycosides in which R comprising $C_8$ and $C_{10}$ alkyl groups (i.e., in the formula (APG-1) n is an integer from 7 to 9) or comprising $C_{12}$- and $C_{14}$ alkyl groups (i.e., in the formula (APG-1) n is an integer from 11 to 13) or comprising $C_8$- to $C_{18}$ alkyl groups, i.e., in the formula (APG-1) n is an integer from 7 to 17), or comprising $C_{12}$- to $C_{16}$ alkyl groups (i.e., in the formula (APG-1), n is an integer from 11 to 15) or comprising $C_{16}$ to $C_{18}$ alkyl groups (i.e., in the formula (APG-1) n is an integer from 15 to 17).

Preferred sugar components are glucose, fructose, galactose, arabinose, and sucrose. It is particularly preferred if Z stands for glucose. In this case, the agent as contemplated herein comprises an alkyl (poly)glucoside.

Quite preferred are the alkyl(poly)glucosides (a1) of the general formula (APG-2)

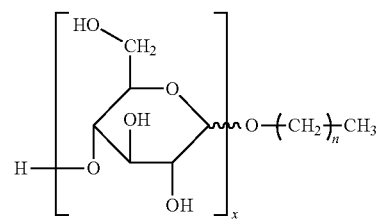

(APG-2)

where x is a number from 1 to 10, preferably a number from 1 to 5, and n is a number from 7 to 29, preferably a number from 7 to 21, further preferably a number from 11 to 21, and most preferably a number from 11 to 17.

In the formula (APG-2), the index number represents a number from 1 to 10, preferably a number from 1 to 5.

The index number n stands for a number from 7 to 29, preferably for a number from 7 to 21, further preferably for a number from 11 to 21 and most preferably for a number from 11 to 17.

In a further embodiment, therefore, a particularly preferred agent as contemplated herein is wherein it comprises:

(a1) comprises at least one alkyl (poly)glucoside of the formula (APG-2),

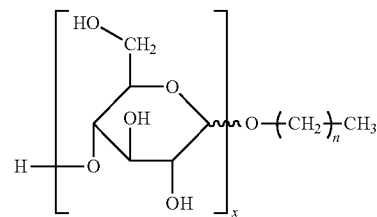

(APG-2)

where x is a number from 1 to 10, preferably a number from 1 to 5, and n is a number from 7 to 29, preferably a number from 7 to 21, further preferably a number from 11 to 21, and most preferably a number from 11 to 17.

The alkyl polyglycosides which can be used as contemplated herein contain on average 1.1 to 5 sugar units. Alkyl polyglycosides with x values of 1.1 to 2.0 are preferred. Alkyl glycosides are particularly preferred, where x averages from 1.1 to 1.8.

Very particularly preferred alkypolyglucosides are those whose alkyl radical is a lauryl radical. In the case of substance mixtures from native sources, preference is given to those sources that have a high proportion of C12 fatty acids, especially coconut fatty acids. Accordingly, particularly preferred agents as contemplated herein are wherein they contain at least one alkyl (poly)glucoside of the formula (APG-2),

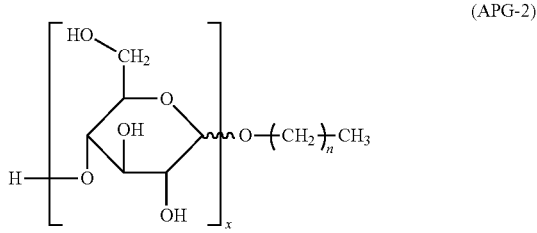

(APG-2)

in which
x is a number from 1.1 to 1.8, very preferably from 1.2 to 1.5, and
n is the number 11.

A particularly suitable alkyl(poly)glucoside of this Tps is, for example, lauryl glucoside, which has the CAS number 110615-47-9 and can be obtained commercially under the trade names Plantacare 1200 UP, Plantaren 1200 UP and Plantaren 1200 N from BASF.

To ensure particularly fine dispersion of the pigments (a2) in the agent of the present disclosure, the alkyl(poly)glycoside(s) (a1) is/are preferably used in certain quantity ranges. Thus, it has been found to be particularly advantageous if the agent comprises—based on the total weight of the agent—one or more alkyl (poly)glycosides (a1) in a total amount of 0.1 to 20.0 wt. %, preferably 0.5 to 15.0 wt. %, more preferably 1.0 to 10.0 wt. %, even more preferably 1.5 to 8.0 wt. %, and most preferably 2.0 to 6.0 wt. %.

In another particularly preferred embodiment, an agent as contemplated herein is wherein it comprises—based on the total weight of the agent—one or more alkyl(poly)glycosides (a1) in a total amount of from 0.1 to 20.0 wt. %, preferably from 0.5 to 15.0 wt. %, more preferably from 1.0 to 10.0 wt. %, still more preferably from 1.5 to 8.0 wt. % and very particularly preferably from 2.0 to 6.0 wt. %.

In a further particularly preferred embodiment, an agent as contemplated herein is wherein it comprises—based on the total weight of the agent—one or more alkyl polyglucosides (a1) in a total amount of from 0.1 to 20.0 wt. %, preferably from 0.5 to 15.0 wt. %, more preferably from 1.0 to 10.0 wt. %, still more preferably from 1.5 to 8.0 wt. % and very particularly preferably from 2.0 to 6.0 wt. %.

Pigments (a2)

As a second essential component, the composition as contemplated herein comprises at least one pigment (a2). Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A beaker glass is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent as contemplated herein is wherein it comprises at least one colorant compound (a2) from the group comprising inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-comprising silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, an agent as contemplated herein is wherein it comprises at least one inorganic pigment (a2) which is preferably selected from the group of colored metal oxides, metal hydroxides, metal oxide hydrates, silicates, metal sulfides, complex metal cyanides, metal sulfates, bronze pigments and/or colored mica- or mica-based pigments coated with at least one metal oxide and/or a metal oxychloride.

In a further preferred embodiment, a composition as contemplated herein is wherein it comprises at least one colorant compound (a2) from the group of pigments selected from mica- or mica-based pigments which are reacted with one or more metal oxides from the group comprising titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:

Colorona Copper, Merck, MICA, CI 77491 (IRON OXIDES)
Colorona Passion Orange, Merck, Mica, CI 77491 (Iron Oxides), Alumina
Colorona Patina Silver, Merck, MICA, CI 77499 (IRON OXIDES), CI 77891 (TITANIUM DIOXIDE)

Colorona RY, Merck, CI 77891 (TITANIUM DIOXIDE), MICA, CI 75470 (CARMINE)

Colorona Oriental Beige, Merck, MICA, CI 77891 (TITANIUM DIOXIDE), CI 77491 (IRON OXIDES)

Colorona Dark Blue, Merck, MICA, TITANIUM DIOXIDE, FERRIC FERROCYANIDE

Colorona Chameleon, Merck, CI 77491 (IRON OXIDES), MICA

Colorona Aborigine Amber, Merck, MICA, CI 77499 (IRON OXIDES), CI 77891 (TITANIUM DIOXIDE)

Colorona Blackstar Blue, Merck, CI 77499 (IRON OXIDES), MICA

Colorona Patagonian Purple, Merck, MICA, CI 77491 (IRON OXIDES), CI 77891 (TITANIUM DIOXIDE), CI 77510 (FERRIC FERROCYANIDE)

Colorona Red Brown, Merck, MICA, CI 77491 (IRON OXIDES), CI 77891 (TITANIUM DIOXIDE)

Colorona Russet, Merck, CI 77491 (TITANIUM DIOXIDE), MICA, CI 77891 (IRON OXIDES)

Colorona Imperial Red, Merck, MICA, TITANIUM DIOXIDE (CI 77891), D&C RED NO. 30 (CI 73360)

Colorona Majestic Green, Merck, CI 77891 (TITANIUM DIOXIDE), MICA, CI 77288 (CHROMIUM OXIDE GREENS)

Colorona Light Blue, Merck, MICA, TITANIUM DIOXIDE (CI 77891), FERRIC FERROCYANIDE (CI 77510)

Colorona Red Gold, Merck, MICA, CI 77891 (TITANIUM DIOXIDE), CI 77491 (IRON OXIDES)

Colorona Gold Plus MP 25, Merck, MICA, TITANIUM DIOXIDE (CI 77891), IRON OXIDES (CI 77491)

Colorona Carmine Red, Merck, MICA, TITANIUM DIOXIDE, CARMINE

Colorona Blackstar Green, Merck, MICA, CI 77499 (IRON OXIDES)

Colorona Bordeaux, Merck, MICA, CI 77491 (IRON OXIDES)

Colorona Bronze, Merck, MICA, CI 77491 (IRON OXIDES)

Colorona Bronze Fine, Merck, MICA, CI 77491 (IRON OXIDES)

Colorona Fine Gold MP 20, Merck, MICA, CI 77891 (TITANIUM DIOXIDE), CI 77491 (IRON OXIDES)

Colorona Sienna Fine, Merck, CI 77491 (IRON OXIDES), MICA

Colorona Sienna, Merck, MICA, CI 77491 (IRON OXIDES)

Colorona Precious Gold, Merck, Mica, CI 77891 (Titanium dioxide), Silica, CI 77491 (Iron oxides), Tin oxide Colorona Sun Gold Sparkle MP 29, Merck, MICA, TITANIUM DIOXIDE, IRON OXIDES, MICA, CI 77891, CI 77491 (EU)

Colorona Mica Black, Merck, CI 77499 (Iron oxides), Mica, CI 77891 (Titanium dioxide)

Colorona Bright Gold, Merck, Mica, CI 77891 (Titanium dioxide), CI 77491 (Iron oxides)

Colorona Blackstar Gold, Merck, MICA, CI 77499 (IRON OXIDES)

Other particularly preferred color pigments with the trade name Xirona® are for example:

Xirona Golden Sky, Merck, Silica, CI 77891 (Titanium Dioxide), Tin Oxide

Xirona Caribbean Blue, Merck, Mica, CI 77891 (Titanium Dioxide), Silica, Tin Oxide Xirona Kiwi Rose, Merck, Silica, CI 77891 (Titanium Dioxide), Tin Oxide Xirona Magic Mauve, Merck, Silica, CI 77891 (Titanium Dioxide), Tin Oxide.

In addition, particularly preferred color pigments with the trade name Unipure® are for example:

Unipure Red LC 381 EM, Sensient CI 77491 (Iron Oxides), Silica

Unipure Black LC 989 EM, Sensient, CI 77499 (Iron Oxides), Silica

Unipure Yellow LC 182 EM, Sensient, CI 77492 (Iron Oxides), Silica

In a further embodiment, the agent as contemplated herein may also contain one or more colorant compounds (a2) from the group comprising organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolo-pyorrole, indigo, thioindido, dioxazine and/or triarylmethane compounds.

Examples of particularly suitable organic pigments are carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In a further particularly preferred embodiment, an agent as contemplated herein is wherein it comprises at least one organic pigment (a2) which is preferably selected from the group of carmine, quinacridone, phthalocyanine, sorghum, blue pigments having the color index numbers Cl 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color lacquer. As contemplated herein, the term color lacquer means particles comprising a layer of absorbed dyes, the unit of particle and dye being insoluble under the above-mentioned conditions. The particles can, for example, be inorganic substrates, which can be aluminum, silica, calcium borosilate, calcium aluminum borosilicate or even aluminum. For example, alizarin color varnish can be used.

Due to their excellent light and temperature resistance, the use of the above-mentioned pigments in the agent as contemplated herein is particularly preferred. It is also preferred if the pigments used have a certain particle size. As contemplated herein, it is therefore advantageous if the at least one pigment has an average particle size $D_{50}$ of 1.0 to 50 µm, preferably 5.0 to 45 µm, preferably 10 to 40 µm, 14 to 30 µm. The average particle size $D_{50}$, for example, can be determined using dynamic light scattering (DLS).

The pigments (a2) represent the second essential of the agent as contemplated herein and are preferably used in the agent in certain ranges of amounts.

Particularly satisfactory results were obtained when the agent included—based on the total weight of the agent—one or more pigments (a2) in a total amount of 0.01 to 10.0 wt. %, preferably 0.1 to 5.0 wt. %, further preferably 0.2 to 2.5 wt. % and very preferably 0.25 to 1.5 wt. %.

In another very particularly preferred embodiment, an agent as contemplated herein is wherein the agent comprises—based on the total weight of the agent—one or more pigments (a2) in a total amount of from 0.01 to 10.0 wt. %, preferably from 0.1 to 5.0 wt. %, more preferably from 0.2 to 2.5 wt. % and very particularly preferably from 0.25 to 1.5 wt. %.

In another very particularly preferred embodiment, an agent as contemplated herein is wherein the agent comprises—based on the total weight of the agent—one or more inorganic pigments (a2) in a total amount of from 0.01 to 10.0% by weight, preferably from 0.1 to 5.0% by weight, more preferably from 0.2 to 2.5% by weight and very particularly preferably from 0.25 to 1.5% by weight.

In another very particularly preferred embodiment, an agent as contemplated herein is wherein the agent comprises—based on the total weight of the agent—one or more organic pigments (a2) in a total amount of from 0.01 to 10.0% by weight, preferably from 0.1 to 5.0% by weight, more preferably from 0.2 to 2.5% by weight and very particularly preferably from 0.25 to 1.5% by weight.

Amino-Functionalized Silicone Polymers (a3)

As a third ingredient essential to the present disclosure, the agent as contemplated herein comprises at least one amino-functionalized silicone polymer (a3). The amino-functionalized silicone polymer may alternatively be referred to as amino silicone or amodimethicone.

Silicone polymers are macromolecules with a molecular weight of at least 500 g/mol, preferably at least 1000 g/mol, more preferably at least 2500 g/mol, particularly preferably at least 5000 g/mol, which comprise repeating organic units.

The maximum molecular weight of the silicone polymer depends on the degree of polymerization (number of polymerized monomers) and the batch size and is partly determined by the polymerization method. For the purposes of the present disclosure, it is preferred if the maximum molecular weight of the silicone polymer is not more than 107 g/mol, preferably not more than 106 g/mol, and particularly preferably not more than 105 g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than 10 Si—O repeat units, preferably more than 50 Si—O repeat units, and more preferably more than 100 Si—O repeat units, most preferably more than 500 Si—O repeat units.

An amino-functionalized silicone polymer is understood to be a functionalized silicone that carries at least one structural unit with an amino group. Preferably, the amino-functionalized silicone polymer carries multiple structural units, each having at least one amino group. An amino group is understood to mean a primary amino group, a secondary amino group, and a tertiary amino group. All these amino groups can be protonated in the acidic environment and are then present in their cationic form.

In principle, beneficial effects could be obtained with amino-functionalized silicone polymers (a3) if they carry at least one primary, at least one secondary and/or at least one tertiary amino group. However, colorations with the highest color intensities were observed when an amino-functionalized silicone polymer (a3) comprising at least one secondary amino group was used in the agent.

In a very particularly preferred embodiment, an agent as contemplated herein is wherein it additionally comprises:
(a3) at least one amino-functionalized silicone polymer having at least one secondary amino group.

The secondary amino group(s) may be located at various positions on the amino-functionalized silicone polymer. Particularly beneficial effects were found when an amino-functionalized silicone polymer (a3) was used that has at least one, preferably several, structural units of the formula (Si amino):

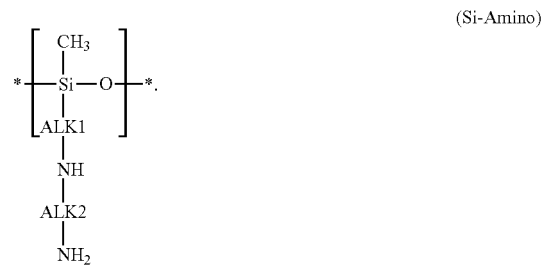

(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, an agent as contemplated herein is wherein the agent comprises at least one amino-functionalized silicone polymer (a3) comprising at least one structural unit of the formula (Si amino):

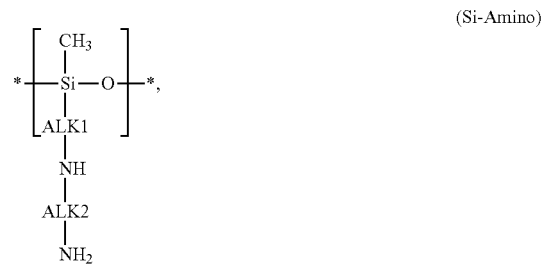

(Si-Amino)

where ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A bivalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—$CH(CH_3)$—) and (—$CH_2$—$CH(CH_3)$—$CH_2$—).

In another particularly preferred embodiment, the structural units of the formula (Si amino) represent repeat units in the amino-functionalized silicone polymer (a3), so that the silicone polymer comprises multiple structural units of the formula (Si amino).

Particularly well-suited amino-functionalized silicone polymers (a3) with at least one secondary amino group are listed below.

Colorations with the very highest color intensities could be obtained when an agent comprising at least one amino-functionalized silicone polymer (a3) comprising structural units of the formula (Si-I) and of the formula (Si-II) was applied to the keratinous material:

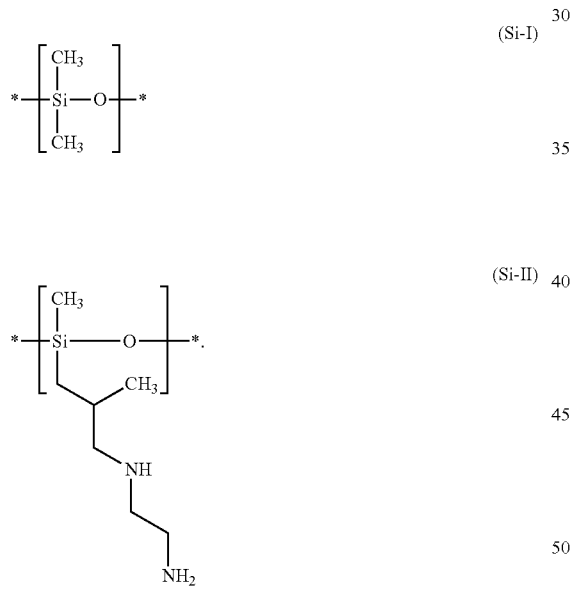

In a further explicitly quite particularly preferred embodiment, an agent as contemplated herein is wherein it comprises at least one amino-functionalized silicone polymer (a3) comprising structural units of the formula (Si-I) and of the formula (Si-II):

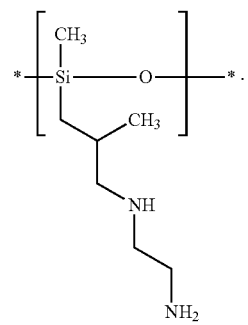

A corresponding amino functionalized silicone polymer with the structural units (Si-I) and (Si-II) is, for example, the commercial product DC 2-8566 or Dowsil 2-8566 Amino Fluid, which is commercially distributed by the Dow Chemical Company and bears the designation "Siloxanes and Silicones, 3-[(2-aminoethyl)amino]-2-methylpropyl Me, Di-Me-Siloxane" and the CAS number 106842-44-8.

In another preferred embodiment, an agent as contemplated herein is wherein it comprises at least one amino-functional silicone polymer (a3) of the formula of the formula (Si-III):

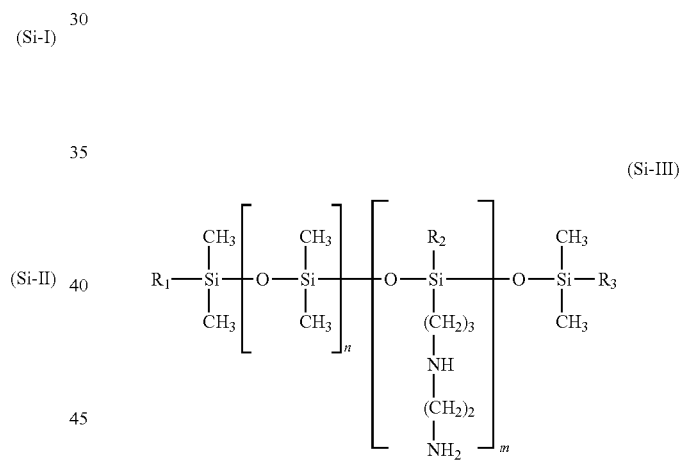

where m and n mean numbers chosen so that the sum (n+m) is in the range 1 to 1000, n is a number in the range 0 to 999 and m is a number in the range 1 to 1000, R1, R2 and R3, which are the same or different, denote a hydroxy group or a C1-4 alkoxy group, wherein at least one of R1 to R3 represents a hydroxy group.

Other compositions preferred as contemplated herein are exemplified by their content of at least one amino-functional silicone polymer (a3) of the formula of the formula (Si-IV), (Si-IV)

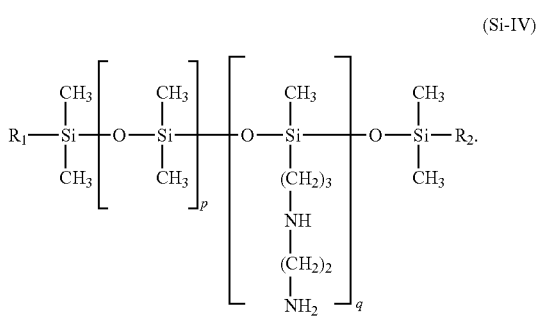

located in the
p and q mean numbers chosen so that the sum (p+q) is in the range 1 to 1000,
p is a number in the range 0 to 999 and q is a number in the range 1 to 1000,
R1 and R2, which are different, denote a hydroxy group or a C1-4 alkoxy group, at least one of R1 to R2 denoting a hydroxy group.

The silicones of the formulas (Si-III) and (Si-IV) differ in the grouping at the Si atom, which carries the nitrogen-comprising group: In formula (Si-III), R2 represents a hydroxy group or a C1-4 alkoxy group, while the radical in formula (Si-IV) is a methyl group. The individual Si groupings, which are marked with the indices m and n or p and q, do not have to be present as blocks; rather, the individual units can also be present in a statistically distributed manner, i.e. in the formulas (Si-III) and (Si-IV), not every R1-Si(CH$_3$)$_2$ group is necessarily bonded to an —[O—Si(CH$_3$)$_2$] grouping.

Agents as contemplated herein which contain at least one amino-functional silicone polymer (a3) of the formula of the formula (Si-V) have also proved to be particularly effective with respect to the desired effects:

(Si-V)

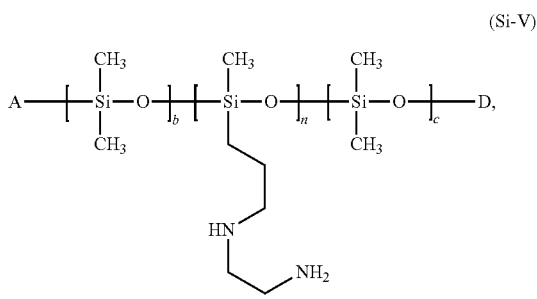

wherein
A represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$,
b, n, and c stand for integers between 0 and 1000,
with the specifications
n>0 and b+c>0, and
at least one of the conditions A═—OH or D═—H is fulfilled.

In the above formula (Si-V), the individual siloxane units are statistically distributed with the indices b, c, and n, i.e., they do not necessarily have to be block copolymers.

Agent (a) may further comprise one or more different amino-functionalized silicone polymers represented by the formula (Si-VI):

$$M(R_aQ_bSiO_{(4-a-b)/2})_x(R_cSiO_{(4-c)/2})_yM \quad \text{(Si-VI)}$$

in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical comprising at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2.000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-comprising radicals, such as mercaptoethyl, mercaptopropyl, mercaptohexyl, mercaptophenyl and the like; preferably R is an alkyl radical comprising from 1 to about 6 carbon atoms, and most preferably R is methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$CH$_2$—, —CH$_2$CH(CH$_3$)C(O)OCH$_2$—, —(CH$_2$)$_3$CC(O)OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—.

Z is an organic amino functional radical comprising at least one amino functional group. One formula for Z is NH(CH$_2$)$_z$NH$_2$, where z is 1 or more. Another formula for Z is —NH(CH$_2$)$_z$(CH$_2$)$_{zz}$NH, wherein both z and zz are independently 1 or more, this structure comprising diamino ring structures, such as piperazinyl. Z is most preferably an —NHCH$_2$CH$_2$NH$_2$ radical. Another formula for Z is —N(CH$_2$)$_z$(CH$_2$)$_{zz}$NX$_2$ or —NX$_2$, wherein each X of X$_2$ is independently selected from the group of hydrogen and alkyl groups having 1 to 12 carbon atoms, and zz is 0.

Q is most preferably a polar, amine-functional radical of the formula —CH$_2$CH$_2$CH$_2$NHCH$_2$CH$_2$NH$_2$. In the formulas, "a" takes values ranging from about 0 to about 2, "b" takes values ranging from about 2 to about 3, "a"+"b" is less than or equal to 3, and "c" is a number ranging from about 1 to about 3. The molar ratio of R$_a$Q$_b$SiO$_{(4-a-b)/2}$ units to R$_c$SiO$_{(4-c)/2}$ units is in the range of about 1:2 to 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In another preferred embodiment, an agent as contemplated herein is wherein it comprises at least one amino-functional silicone polymer of the formula (Si-VII),

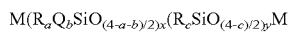 (Si-VII), wherein:
G is -H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, —C(CH$_3$)$_3$;
a stands for a number between 0 and 3, especially 0.
b stands for a number between 0 and 1, especially 1,
m and n are numbers whose sum (m+n) is between 1 and 2000, preferably between 50 and 150, where n preferably assumes values from 0 to 1999 and from 49 to 149 and m preferably assumes values from 1 to 2000, from 1 to 10,
R' is a monovalent radical selected from
-Q-N(R")—CH$_2$—CH$_2$—N(R")$_2$
-Q-N(R")$_2$
-Q-N+(R")$_3$A$^-$
-Q-N+H(R")$_2$A$^-$
-Q-N+H$_2$(R")A$^-$
-Q-N(R")—CH$_2$—CH$_2$—N$^+$R"H$_2$A$^-$,
where each Q is a chemical bond, —CH$_2$—, —CH$_2$—CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, —CH(CH$_3$)CH$_2$CH$_2$—,
R" represents identical or different radicals selected from the group of —H, -phenyl, -benzyl, —CH$_2$—CH(CH$_3$)Ph, the C$_{1-20}$ alkyl radicals, preferably —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, and A represents an anion preferably selected from chloride, bromide, iodide or methosulfate.

In the context of a further preferred embodiment, an agent as contemplated herein is wherein it comprises at least one amino-functional silicone polymer (a3) of the formula (Si-VIIa):

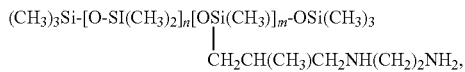

(SI-VIIa)

wherein m and n are numbers whose sum (m+n) is between 1 and 2000, preferably between 50 and 150, n preferably assuming values from 0 to 1999 and from 49 to 149, and m preferably assuming values from 1 to 2000, from 1 to 10.

According to the INCI declaration, these silicones are called trimethylsilylamodimethicones.

In the context of a further preferred embodiment, an agent as contemplated herein is wherein it comprises at least one amino-functional silicone polymer of the formula (Si-VIIb)

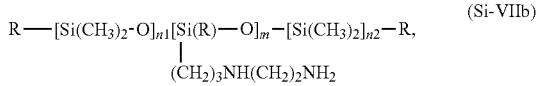

(Si-VIIb)

in which R represents —OH, —O—CH$_3$ or a —CH$_3$ group and m, n1 and n2 are numbers whose sum (m+n1+n2) is between 1 and 2000, preferably between 50 and 150, the sum (n1+n2) preferably assuming values from 0 to 1999 and in particular from 49 to 149 and m preferably assuming values from 1 to 2000, in particular from 1 to 10.

According to the INCI declaration, these amino-functionalized silicone polymers are called amodimethicones.

Regardless of which amino-functional silicones are used, agents as contemplated herein are preferred which contain an amino-functional silicone polymer (a3) whose amine number is above 0.25 meq/g, preferably above 0.3 meq/g and above 0.4 meq/g. The amine number represents the milliequivalents of amine per gram of the amino-functional silicone. It can be determined by titration and expressed in the unit mg KOH/g.

Furthermore, agents comprising a special 4-morpholinomethyl-substituted silicone polymer (a3) are also suitable. This amino-functionalized silicone polymer comprises structural units of the formulae (SI-VIII) and of the formula (Si-IX)

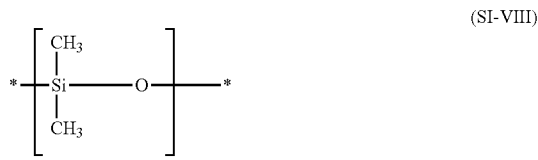

(SI-VIII)

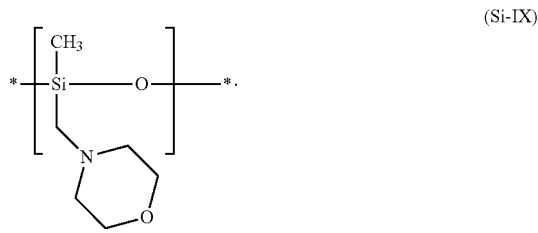

(Si-IX)

Corresponding 4-morpholinomethyl-substituted silicone polymers are described below.

A preferred amino-functionalized silicone polymer is known as. Amodimethicone/Morpholinomethyl Silsesquioxane Copolymer is known and commercially available from Wacker in the form of the raw material Belsil ADM 8301 E.

As a 4-morpholinomethyl-substituted silicone, for example, a silicone can be used which has structural units of the formulae (Si-VIII), (Si-IX) and (Si-X):

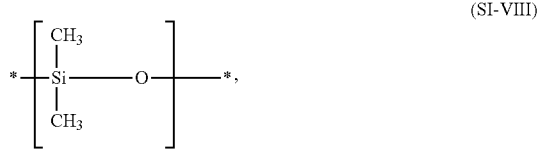

(SI-VIII)

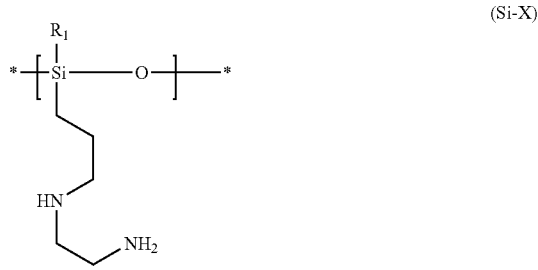

(Si-X)

-continued (Si-IX)

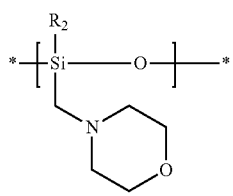

in which
R1 is —CH$_3$, —OH, —OCH$_3$, —O—CH$_2$CH$_3$, —O—CH$_2$CH$_2$CH$_3$, or —O—CH(CH$_3$)$_2$, and
R2 is —CH$_3$, —OH, or —OCH$_3$.

Particularly preferred compositions as contemplated herein contain at least one 4-morpholinomethyl-substituted silicone of the formula (Si-XI):

(Si-XI)

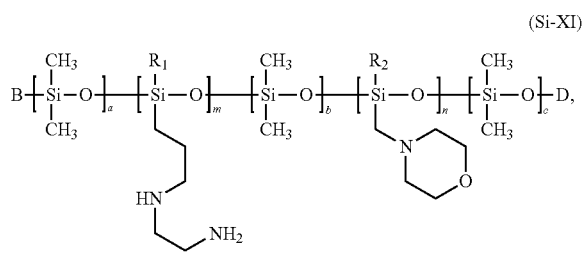

wherein
R1 is —CH$_3$, —OH, —OCH$_3$, —O—CH$_2$CH$_3$, —O—CH$_2$CH$_2$CH$_3$, or —O—CH(CH$_3$)$_2$.
R2 is —CH$_3$, —OH, or —OCH$_3$.
B represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$,
a, b, and c stand independently for integers between 0 and 1000, with the condition a+b+c>0,
m and n independently of each other stand for integers between 1 and 1000,
with the proviso that
at least one of the conditions B═—OH or D═—H is fulfilled,
the units a, b, c, m, and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m, and n are preferably statistically distributed.

The silicones used as contemplated herein represented by formula (Si-VI) can be trimethylsilyl-terminated (D or B═—Si(CH$_3$)$_3$), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which
B═—O—Si(CH$_3$)$_2$OH and D═—Si(CH$_3$)$_3$,
B═—O—Si(CH$_3$)$_2$OH and D═—Si(CH$_3$)$_2$OH
B═—O—Si(CH$_3$)$_2$OH and D═—Si(CH$_3$)$_2$OCH$_3$,
B═—O—Si(CH$_3$)$_3$ and D═—Si(CH$_3$)$_2$OH, and
B═—O—Si(CH$_3$)$_2$OCH$_3$ and D═—Si(CH$_3$)$_2$OH.

These silicones lead to exorbitant improvements in the hair properties of the hair treated with the agents of the present disclosure, and to a seriously improved protection in oxidative treatment.

It has been found to be particularly advantageous if the agent as contemplated herein comprises the amino-functionalized silicone polymer(s) (a3) in certain quantity ranges. Particularly satisfactory results were obtained when the agent included—based on the total weight of the agent—a total amount of 0.1 to 8.0 wt. %, preferably 0.2 to 5.0 wt. %, more preferably 0.3 to 3.0 wt. %, and most preferably 0.4 to 2.5 wt. %.

In another particularly preferred embodiment, an agent as contemplated herein is wherein it comprises—based on the total weight of the agent—one or more amino-functionalized silicone polymers (a3) in a total amount of from 0.1 to 8.0 wt. %, preferably from 0.2 to 5.0 wt. %, more preferably from 0.3 to 3.0 wt. % and very particularly preferably from 0.4 to 2.5 wt. %.

Other Optional Components in the Agent

Depending on the desired form of packaging, the agent as contemplated herein may optionally also contain other components or ingredients.

Fat Components in the Agent

If the agent is to be provided in the form of an emulsion or cream, the use of at least one fat constituent has proved particularly advantageous. The fatty components are hydrophobic substances that can form emulsions in the presence of water, forming micelle systems. Without being committed to this theory, it is assumed that the C$_1$-C$_6$ alkoxysilanes—either in the form of their monomers or in the form of their condensed oligomers—are embedded in this hydrophobic environment or in the micelle systems so that the polarity of their environment changes. Due to the hydrophobic character of the fatty components, the environment of the C$_1$-C$_6$ alkoxysilanes is also hydrophobised. It is assumed that the polymerization reaction of the C$_1$-C$_6$ alkoxy silanes leading to the film or coating takes place in an environment of reduced polarity at reduced speed.

For the purposes of the present disclosure, "fatty components" means organic compounds with a solubility in water at room temperature (22° C.) and atmospheric pressure (760 mmHg) of less than 1 wt. %, preferably less than 0.1 wt. %. The definition of fat constituents explicitly covers only uncharged (i.e., non-ionic) compounds. Fat components have at least one saturated or unsaturated alkyl group with at least 12 C atoms. The molecular weight of the fat constituents is a maximum of 5000 g/mol, preferably a maximum of 2500 g/mol and particularly preferably a maximum of 1000 g/mol. The fat components are neither polyoxyalkylated nor polyglycerylated compounds.

Very preferably, the additional fatty components used in the composition can be selected from the group of C$_{12}$-C$_{30}$ fatty alcohols, C$_{12}$-C$_{30}$ fatty acid triglycerides, C$_{12}$-C$_{30}$ fatty acid monoglycerides, C$_{12}$-C$_{30}$ fatty acid diglycerides and/or hydrocarbons.

In the context of a further preferred embodiment, an agent as contemplated herein is wherein it comprises one or more fat constituents from the group comprising the C$_{12}$-C$_{30}$ fatty alcohols, the C$_{12}$-C$_{30}$ fatty acid triglycerides, the C$_{12}$-C$_{30}$ fatty acid monoglycerides, the C$_{12}$-C$_{30}$ fatty acid diglycerides and/or the hydrocarbons.

In this context, very particularly preferred fat constituents are understood to be constituents from the group of C$_{12}$-C$_{30}$ fatty alcohols, C$_{12}$-C$_{30}$ fatty acid triglycerides, C$_{12}$-C$_{30}$ fatty acid monoglycerides, C$_{12}$-C$_{30}$ fatty acid diglycerides and/or hydrocarbons. For the purposes of the present disclosure, only non-ionic substances are explicitly regarded as fat components. Charged compounds such as fatty acids and their salts are not considered to be fat components.

The $C_{12}$-$C_{30}$ fatty alcohols can be saturated, mono- or polyunsaturated, linear, or branched fatty alcohols with 12 to 30 C atoms.

Examples of preferred linear, saturated C12-C30 fatty alcohols are dodecan-1-ol (dodecyl alcohol, lauryl alcohol), tetradecan-1-ol (tetradecyl alcohol, myristyl alcohol), hexadecan-1-ol (hexadecyl alcohol, Cetyl alcohol, palmityl alcohol), octadecan-1-ol (octadecyl alcohol, stearyl alcohol), arachyl alcohol (eicosan-1-ol), heneicosyl alcohol (heneicosan-1-ol) and/or behenyl alcohol (docosan-1-ol).

Preferred linear unsaturated fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenoyl alcohol), gadoleyl alcohol ((9Z)-eicos-9-en-1-ol), arachidone alcohol ((5Z,8Z,11Z,14Z)-eicosa-5,8,11,14-tetraen-1-ol), erucyl alcohol ((13Z)-docos-13-en-1-ol) and/or brassidyl alcohol ((13E)-docosen-1-ol).

The preferred representatives for branched fatty alcohols are 2-octyl-dodecanol, 2-hexyl-dodecanol and/or 2-butyl-dodecanol. In a further preferred embodiment, an agent as contemplated herein is wherein it comprises one or more $C_{12}$-$C_{30}$ fatty alcohols (a4) selected from:

Dodecan-1-ol (dodecyl alcohol, lauryl alcohol),
Tetradecan-1-ol (tetradecyl alcohol, myristyl alcohol),
Hexadecan-1-ol (hexadecyl alcohol, cetyl alcohol, palmityl alcohol),
Octadecan-1-ol (octadecyl alcohol, stearyl alcohol),
Arachyl alcohol (eicosan-1-ol),
Heneicosyl alcohol (heneicosan-1-ol),
Behenyl alcohol (docosan-1-ol),
(9Z)-Octadec-9-en-1-ol (oleyl alcohol),
(9E)-Octadec-9-en-1-ol (elaidyl alcohol),
(9Z,12Z)-Octadeca-9,12-dien-1-ol (linoleyl alcohol),
(9Z,12Z,15Z)-Octadeca-9,12,15-trien-1-ol (linolenoyl alcohol),
Gadoleyl alcohol ((9Z)-Eicos-9-en-1-ol),
Arachidonic alcohol ((5Z,8Z,11Z,14Z)-Eicosa-5,8,11,14-tetraen-1-ol),
Erucyl alcohol ((13Z)-docos-13-en-1-ol),
Brassidyl alcohol ((13E)-docosen-1-ol),
2-Octyl-dodecanol,
2-hexyl dodecanol and/or
2-Butyl-dodecanol comprises.

It has been found to be quite preferable to use one or more $C_{12}$-$C_{30}$ fatty alcohols in quite specific ranges of amounts.

Furthermore, it is particularly preferred if the composition comprises one or more $C_{12}$-$C_{30}$ fatty alcohols in a total amount of from 2.0 to 50.0% by weight, preferably from 3.0 to 30.0% by weight, more preferably from 4.0 to 20.0% by weight, still more preferably from 5.0 to 15.0% by weight and most preferably from 5.0 to 10.0% by weight, based on the total weight of the composition.

Further, as a suitable fat ingredient, the agent may also contain at least one $C_{12}$-$C_{30}$ fatty acid triglyceride that is $C_{12}$-$C_{30}$ fatty acid monoglyceride and/or $C_{12}$-$C_{30}$ fatty acid diglyceride. For the purposes of the present disclosure, a $C_{12}$-$C_{30}$ fatty acid triglyceride is understood to be the triester of the trivalent alcohol glycerol with three equivalents of fatty acid. Both structurally identical and different fatty acids within a triglyceride molecule can be involved in the formation of esters.

As contemplated herein, fatty acids are to be understood as saturated or unsaturated, unbranched, or branched, unsubstituted or substituted $C_{12}$-$C_{30}$ carboxylic acids. Unsaturated fatty acids can be mono- or polyunsaturated. For an unsaturated fatty acid, its C—C double bond(s) may have the Cis or Trans configuration.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

The fatty acid triglycerides can also be of natural origin. The fatty acid triglycerides or mixtures thereof occurring in soybean oil, peanut oil, olive oil, sunflower oil, macadamia nut oil, moringa oil, apricot kernel oil, marula oil and/or optionally hardened castor oil are particularly suitable for use in the product as contemplated herein.

A $C_{12}$-$C_{30}$ fatty acid monoglyceride is understood to be the monoester of the trivalent alcohol glycerol with one equivalent of fatty acid. Either the middle hydroxy group of glycerol or the terminal hydroxy group of glycerol may be esterified with the fatty acid.

$C_{12}$-$C_{30}$ fatty acid monoglycerides are particularly suitable in which a hydroxyl group of glycerol is esterified with a fatty acid, the fatty acids being selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], or nervonic acid [(15Z)-tetracos-15-enoic acid].

A $C_{12}$-$C_{30}$ fatty acid diglyceride is the diester of the trivalent alcohol glycerol with two equivalents of fatty acid. Either the middle and one terminal hydroxy group of glycerol may be esterified with two equivalents of fatty acid, or both terminal hydroxy groups of glycerol are esterified with one fatty acid each. The glycerol can be esterified with two structurally identical fatty acids or with two different fatty acids.

Fatty acid triglycerides are particularly suitable in which at least one of the ester groups is formed from glycerol with a fatty acid selected from dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), petroselinic acid [(Z)-6-octadecenoic acid], palmitoleic acid [(9Z)-hexadec-9-enoic acid], oleic acid [(9Z)-octadec-9-enoic acid], elaidic acid [(9E)-octadec-9-enoic acid], erucic acid [(13Z)-docos-13-enoic acid], linoleic acid [(9Z, 12Z)-octadeca-9,12-dienoic acid, linolenic acid [(9Z, 12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid], and/or nervonic acid [(15Z)-tetracos-15-enoic acid].

Particularly good results were obtained when the composition included at least one $C_{12}$-$C_{30}$ fatty acid monoglyceride selected from the monoesters of glycerol with one equivalent of fatty acid selected from the group of dodecanoic acid (lauric acid), tetradecanoic acid (myristic acid), hexadecanoic acid (palmitic acid), tetracosanoic acid (lignoceric acid), octadecanoic acid (stearic acid), eicosanoic acid (arachidic acid), docosanoic acid (behenic acid), Petroselic acid [(Z)-6-octadecenoic acid], Palmitoleic acid [(9Z)-Hexadec-9-enoic acid], Oleic acid [(9Z)-Octadec-9-enoic acid], Elaidic acid [(9E)-Octadec-9-enoic acid], Erucic acid [(13Z)-Docos-13-enoic acid], Linoleic acid [(9Z, 12Z)-Octadeca-9, 12-dienoic acid, linolenic acid [(9Z,12Z,15Z)-octadeca-9,12,15-trienoic acid, elaeostearic acid [(9Z,11E,13E)-octadeca-9,11,3-trienoic acid], arachidonic acid [(5Z,8Z,11Z,14Z)-icosa-5,8,11,14-tetraenoic acid] and/or nervonic acid [(15Z)-tetracos-15-enoic acid].

In the context of a further embodiment, an agent as contemplated herein is wherein it comprises at least one $C_{12}$-$C_{30}$ fatty acid monoglyceride selected from the monoesters of glycerol with one equivalent of fatty acid from the group comprising dodecanoic acid, tetradecanoic acid, hexadecanoic acid, tetracosanoic acid, octadecanoic acid, eicosanoic acid and/or docosanoic acid.

It has been shown to be preferable to use one or more $C_{12}$-$C_{30}$ fatty acid mono-, $C_{12}$-$C_{30}$ fatty acid di- and/or $C_{12}$-$C_{30}$ fatty acid triglycerides (a4) in specific ranges of amounts in the composition.

With regard to the solution of the problem as contemplated herein, it has proved advantageous if the composition—based on the total weight of the composition—included one or more $C_{12}$-$C_{30}$ fatty acid mono-, $C_{12}$-$C_{30}$ fatty acid di- and/or $C_{12}$-$C_{30}$ fatty acid triglycerides (a4) in a total amount of 0.1 to 20.0 wt.-%, preferably from 0.3 to 15.0 wt. %, more preferably from 0.5 to 10.0 wt. % and most preferably from 0.8 to 5.0 wt. %.

In a very particularly preferred embodiment, a process as contemplated herein is wherein the composition comprises—based on the total weight of the composition—one or more $C_{12}$-$C_{30}$ fatty acid mono-, $C_{12}$-$C_{30}$ fatty acid di- and/or $C_{12}$-$C_{30}$ fatty acid triglycerides in a total amount of from 0.1 to 20.0% by weight, preferably from 0.3 to 15.0% by weight, more preferably from 0.5 to 10.0% by weight and very particularly preferably from 0.8 to 5.0% by weight.

The $C_{12}$-$C_{30}$ fatty acid mono-, $C_{12}$-$C_{30}$ fatty acid di- and/or $C_{12}$-$C_{30}$ fatty acid triglycerides may be used as the sole fat components (a4) in the compositions. However, it may also be suitable as contemplated herein to incorporate at least one $C_{12}$-$C_{30}$ fatty acid mono-, $C_{12}$-$C_{30}$ fatty acid di- and/or $C_{12}$-$C_{30}$ fatty acid triglyceride in combination with at least one $C_{12}$-$C_{30}$ fatty alcohol into the composition.

Furthermore, as a very particularly preferred fat constituent, the agents may also contain at least one hydrocarbon.

Hydrocarbons are compounds comprising exclusively of the atoms carbon and hydrogen with 8 to 80 C atoms. In this context, aliphatic hydrocarbons such as mineral oils, liquid paraffin oils (e.g., Paraffinium Liquidum or Paraffinum Perliquidum), isoparaffin oils, semi-solid paraffin oils, paraffin waxes, hard paraffin (Paraffinum Solidum), vaseline and polydecenes are particularly preferred.

Liquid paraffin oils (Paraffinum Liquidum and Paraffinium Perliquidum) have proven to be particularly suitable in this context. Paraffinum Liquidum, also known as white oil, is the preferred hydrocarbon. Paraffinum Liquidum is a mixture of purified, saturated, aliphatic hydrocarbons, comprising hydrocarbon chains with a C-chain distribution of 25 to 35 C-atoms.

Particularly satisfactory results were obtained when the agent included at least one hydrocarbon selected from the group of mineral oils, liquid kerosene oils, isoparaffin oils, semisolid kerosene oils, kerosene waxes, hard kerosene (paraffinum solidum), petrolatum and polydecenes.

In a very particularly preferred embodiment, an agent as contemplated herein is wherein it comprises at least one fatty constituent from the group of hydrocarbons.

With regard to the solution of the problem as contemplated herein, it proved to be quite particularly preferable if the agent included—based on the total weight of the composition—one or more hydrocarbons in a total amount of from 0.5 to 20.0 wt. %, preferably from 0.7 to 10.0 wt. %, more preferably from 0.9 to 5.0 wt. % and very particularly preferably from 1.0 to 4.0 wt. %.

Water Content in Agent

The agent described above is a ready-to-use agent that can be applied to the keratinous material. This ready-to-use agent preferably has a high-water content. It has been found that particularly suitable agents are those comprising—based on the total weight of the agent—50.0 to 98.0 wt. %, preferably 60.0 to 90.0 wt. %, more preferably 70.0 to 90.0 wt. % and most preferably 75.0 to 90.0 wt. % of water.

In a further explicitly quite particularly preferred embodiment, an agent as contemplated herein is wherein it comprises—based on the total weight of the agent—50.0 to 98.0 wt. %, preferably 60.0 to 90.0 wt. %, further preferably 70.0 to 90.0 wt. % and very particularly preferably 75.0 to 90.0 wt. % of water.

Other Surfactants in the Agent

Due to the optional but preferred content of water and fat constituent, the agent as contemplated herein is particularly preferably in the form of an emulsion. To further optimize the formation of the emulsion, it may prove preferable to continue to use in the agent at least one further surfactant which is different from the alkyl (poly)glycosides (a1).

The term surfactants (T) refer to surface-active substances that can form adsorption layers on surfaces and interfaces or aggregate in bulk phases to form micelle colloids or lyotropic mesophases. A distinction is made between anionic surfactants comprising a hydrophobic radical and a negatively charged hydrophilic head group, amphoteric surfactants, which carry both a negative and a compensating positive charge, cationic surfactants, which have a positively charged hydrophilic group in addition to a hydrophobic radical, and non-ionic surfactants, which have no charges but strong dipole moments and are strongly hydrated in aqueous solution.

In a very particularly preferred embodiment, an agent as contemplated herein is wherein it comprises at least one nonionic surfactant.

Non-ionic surfactants contain, for example, a polyol group, a polyalkylene glycol ether group or a combination of polyol and polyglycol ether group as the hydrophilic group. Such links include Addition products of 2 to 50 mol ethylene oxide and/or 0 to 5 mol propylene oxide to linear and branched fatty alcohols with 6 to 30 C atoms, the fatty alcohol polyglycol ethers or the fatty alcohol polypropylene glycol ethers or mixed fatty alcohol polyethers, Addition products of 2 to 50 mol ethylene oxide and/or 0 to 5 mol propylene oxide to linear and branched fatty acids with 6 to 30 C atoms, the fatty acid polyglycol ethers or the fatty acid polypropylene glycol ethers or mixed fatty acid polyethers, Addition products of 2 to 50 mol ethylene oxide and/or 0 to 5 mol propylene oxide to linear and branched alkylphenols having 8 to 15 C atoms in the alkyl group, the alkylphenol polyglycol ethers or the alkylpolypropylene glycol ethers or mixed alkylphenol polyethers, with a methyl or $C_2$-$C_6$-alkyl radical end-group capped addition products of 2 to 50 moles of ethylene oxide and/or 0 to 5 moles of propylene oxide to linear and branched fatty alcohols with 8 to 30 C atoms, to fatty acids with 8 to 30 C atoms and to alkylphenols with 8 to 15 C atoms in the alkyl group, such as the grades available under the sales names Dehydol® LS, Dehydol® LT (Cognis), C12-C30 fatty acid mono- and diesters of addition products of 1 to 30 mol ethylene oxide to glycerol, Addition products of 5 to 60 mol ethylene oxide to castor oil and hardened castor oil, Polyol fatty acid esters, such as the commercial product Hydagen® HSP (Cognis) or Sovermol® grades (Cognis), alkoxylated triglycerides, alkoxylated fatty acid alkyl esters of the formula (Tnio-1)

$R^1CO$—$(OCH_2CHR^2)_wOR^3$ (Tnio-1)

in which $R^1CO$ is a linear or branched, saturated and/or unsaturated acyl radical having 6 to 22 carbon atoms, R2 is hydrogen or methyl, $R^3$ is linear or branched alkyl radicals having 1 to 4 carbon atoms and w is numbers from 1 to 20, amine oxides, Hydroxy mixed ethers, as described for example in DE-OS 19738866, Sorbitan fatty acid esters and addition products of ethylene oxide to sorbitan fatty acid esters such as polysorbates, Addition products of ethylene oxide to fatty acid alkanolamides and fatty amines, Other typical examples of nonionic surfactants are fatty acid amide polyglycol ethers, fatty amine polyglycol ethers, mixed ethers or mixed formals, protein hydrolysates (especially wheat-based vegetable products) and polysorbates.

The alkylene oxide addition products to saturated linear fatty alcohols and fatty acids, each with 2 to 30 moles of ethylene oxide per mole of fatty alcohol or fatty acid, and the sugar surfactants have proved to be preferred nonionic surfactants. Preparations with excellent properties are also obtained if they contain fatty acid esters of ethoxylated glycerol as non-ionic surfactants.

These connections are identified by the following parameters. The alkyl radical R comprises 6 to 22 carbon atoms and can be either linear or branched. Primary linear and in 2-position methyl-branched aliphatic radicals are preferred. Such alkyl radicals are for example 1-octyl, 1-decyl, 1-lauryl, 1-myristyl, 1-cytyl and 1-stearyl. Especially preferred are 1-octyl, 1-decyl, 1-lauryl, 1-myristyl. When so-called "oxo-alcohols" are used as starting materials, compounds with an odd number of carbon atoms in the alkyl chain predominate.

The compounds with alkyl groups used as surfactants can each be uniform substances. However, it is usually preferable to start from native plant or animal raw materials in the production of these substances, so that one obtains substance mixtures with different alkyl chain lengths depending on the respective raw material.

For surfactants which are products of the addition of ethylene and/or propylene oxide to fatty alcohols or derivatives of these addition products, both products with a "normal" homologue distribution and those with a narrowed homologue distribution can be used. By "normal" homologue distribution we mean mixtures of homologues obtained in the reaction of fatty alcohol and alkylene oxide using alkali metals, alkali metal hydroxides or alkali metal alcoholates as catalysts. Constricted homologue distributions are obtained, on the other hand, when, for example, hydrotalcites, alkaline earth metal salts of ether carboxylic acids, alkaline earth metal oxides, hydroxides or alcoholates are used as catalysts. The use of products with narrowed homologue distribution may be preferred.

Particularly satisfactory results were obtained when an agent (b) comprising at least one ethoxylated fatty alcohol with a degree of ethoxylation of 80 to 120 was used in the process as contemplated herein.

In another very particularly preferred embodiment, an agent as contemplated herein is wherein it comprises at least one nonionic surfactant of the formula (T-I):

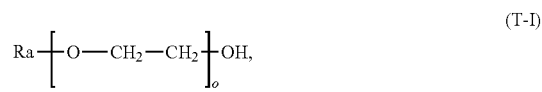

$$Ra \left[O-CH_2-CH_2\right]_o OH, \quad (T\text{-}I)$$

wherein Ra represents a saturated or unsaturated, straight, or branched $C_8$-$C_{24}$ alkyl group, preferably a saturated, straight $C_{16}$-bis $C_{18}$ alkyl group, and o is an integer from 80 to 120, preferably an integer from 90 to 110, and particularly preferably the number 100.

A particularly well-suited non-ionic surfactant of this type bears the trade name Brij S 100 or Brij S 100 PA SG. This is stearyl alcohol, ethoxylated with 100 EO, which is commercially available from Croda and has the CAS number 9005-00-9.

Furthermore, particularly satisfactory results were obtained when an agent as contemplated herein was used which included at least one ethoxylated fatty alcohol with a degree of ethoxylation of 10 to 40.

In another very particularly preferred embodiment, an agent as contemplated herein is wherein it comprises at least one nonionic surfactant of the formula (T-II):

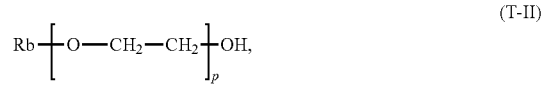

$$Rb \left[O-CH_2-CH_2\right]_p OH, \quad (T\text{-}II)$$

wherein
Ra is a saturated or unsaturated, unbranched, or branched $C_8$-$C_{24}$ alkyl group, preferably a saturated, unbranched $C_{16}$- to $C_{18}$ alkyl group, and
p an integer from 10 to 40, preferably an integer from 20 to 35, and particularly preferably the number 30.

A particularly well-suited non-ionic surfactant of this type is ceteareth-30. Ceteareth-30 is a mixture of cetyl alcohol and stearyl alcohol, each ethoxylated with 30 units of ethylene oxide. The mixture of cetyl alcohol and stearyl alcohol is called cetearyl alcohol. Ceteareth-30 has the CAS number 68439-49-6 and can be purchased, for example, under the trade name Eumulgin B3 from BASF.

It has been found to be quite preferred if the composition comprises both at least one non-ionic surfactant of formula (T-I) and at least one non-ionic surfactant of formula (T-II).

Medium Solvent

The use of solvents has continued to produce particularly satisfactory results. For this reason, the composition as contemplated herein may additionally contain at least one solvent as an optional component.

Suitable solvents may include, for example, solvents selected from the group of 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol and benzyl alcohol. The use of 1,2-propylene glycol is particularly preferred.

In another very particularly preferred embodiment, a composition as contemplated herein is wherein it comprises at least one solvent selected from the group of 1,2-propylene glycol, 1,3-propylene glycol, ethylene glycol, 1,2-butylene glycol, dipropylene glycol, ethanol, isopropanol, diethylene glycol monoethyl ether, glycerol, phenoxyethanol and benzyl alcohol, very preferably 1,2-propylene glycol.

1,2-Propylene glycol is alternatively referred to as 1,2-propanediol and bears the CAS numbers 57-55-6 [(RS)-1,2-dihydroxypropane], 4254-14-2 [(R)-1,2-dihydroxypropane] and 4254-153 [(S)-1,2-dihydroxypropane]. Ethylene glycol is alternatively known as 1,2-ethanediol and carries CAS number 107-21-1. Glycerol is alternatively known as 1,2,3-propanetriol and carries CAS number 56-81-5. Phenoxyethanol has the Cas number 122-99-6.

All the solvents described previously are commercially available from various chemical suppliers, such as Aldrich or Fluka.

By using the above-mentioned solvents in suitable application quantities, a particularly stable agent can be obtained, with which color results of remarkably high intensity can be obtained on the keratinous material.

In a further preferred embodiment, an agent as contemplated herein is wherein it comprises—based on the total weight of the agent—one or more solvents in a total amount of 1.0 to 20.0% by weight, preferably 2.0 to 15.0% by weight, more preferably 3.0 to 15.0% by weight and very particularly preferably 4.0 to 10.0% by weight of 1,2-propylene glycol.

Polymers in the Agent

The agent as contemplated herein may additionally comprise at least one film-forming polymer. The film-forming polymer may be selected, for example, from the group comprising polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, explicitly very particularly preferred polyvinylpyrrolidone (PVP).

Further suitable film-forming polymers can be selected from the group of copolymers of acrylic acid, copolymers of methacrylic acid, homopolymers or copolymers of acrylic acid esters, homopolymers or copolymers of methacrylic acid esters, homopolymers or copolymers of acrylic acid amides, homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming polymers selected from the group of synthetic polymers, polymers obtainable by free-radical polymerization, or natural polymers have proven to be well suited.

Other particularly well-suited film-forming polymers can be selected from the homopolymers or copolymers of olefins, such as cycloolefins, butadiene, isoprene or styrene, vinyl ethers, vinyl amides, the esters, or amides of (meth) acrylic acid having at least one $C_1$-$C_{20}$ alkyl group, an aryl group or a C2-C10 hydroxyalkyl group.

Other film-forming polymers may be selected from the homo- or copolymers of isooctyl (meth)acrylate; isononyl (meth)acrylate; 2-ethylhexyl (meth)acrylate; lauryl (meth) acrylate); isopentyl (meth)acrylate; n-butyl (meth)acrylate); isobutyl (meth)acrylate; ethyl (meth)acrylate; methyl (meth) acrylate; tert-butyl (meth)acrylate; stearyl (meth)acrylate; hydroxyethyl (meth)acrylate; 2-hydroxypropyl (meth)acrylate; 3-hydroxypropyl (meth)acrylate; and/or mixtures thereof.

Further film-forming polymers may be selected from the homo- or copolymers of (meth)acrylamide; N-alkyl-(meth) acrylamides, in those with C2-C18 alkyl groups, such as N-ethyl-acrylamide, N-tert-butyl-acrylamide, le N-octyl-crylamide; N-di(C1-C4)alkyl-(meth)acrylamide.

Other suitable anionic copolymers include copolymers of acrylic acid, methacrylic acid or their $C_1$-$C_6$ alkyl esters, as sold under the INCI declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Polymers on the market include Aculyn® 22 (Acrylate/Steareth-20 Me-thacrylate Copolymer), Aculyn® 28 (Acrylate/Beheneth-25 Methacrylate Copolymer), Structure 2001@(Acryla-tes/Steareth-20 Itaconate Copolymer), Structure 3001@ (Acrylate/Ceteth-20 Itaconate Copolymer), Structure Plus® (acrylate/aminoacrylate C10-30 alkyl PEG-20 itaconate copolymer), Carbopol® 1342, 1382, Ultrez 20, Ultrez 21 (acrylate/C10-30 alkyl acrylate cross polymer), Synthalen W 2000® (acrylate/palmeth-25 acrylate copolymer) or Soltex OPT (acrylate/C12-22 alkyl methacrylate copolymer) distributed by Rohme und Haas.

The homo- and copolymers of N-vinylpyrrolidone, vinylcaprolactam, vinyl-(C1-C6)alkyl-pyrrole, vinyl-oxazole, vinyl-thiazole, vinylpyrimidine, vinylimidazole can be named as suitable polymers based on vinyl monomers.

Also suitable are the copolymers octylacrylamide/acrylates/butylaminoethyl methacrylate copolymer, such as those sold commercially under the trade names AMPHOMER® or LOVOCRYL® 47 from NATIONAL STARCH, or the copolymers of acrylates/octylacrylamides sold under the trade names DERMACRYL® LT and DERMACRYL® 79 from NATIONAL STARCH.

Suitable olefin-based polymers include homopolymers and copolymers of ethylene, propylene, butene, isoprene and butadiene.

In another embodiment, the film-forming hydrophobic polymers may be the block copoylmers comprising at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

The agents may also contain other active ingredients, auxiliaries and additives, such as solvents, structurants such as glucose, maleic acid and lactic acid, hair-conditioning compounds such as phospholipids, for example lecithin and cephalins; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; Ceramides or pseudoceramides; vitamins, provitamins and vitamin precursors; plant extracts; fats and waxes such as fatty alcohols, beeswax, montan wax and kerosene; Swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3-distearate; and blowing agents such as propane-butane mixtures, $N_2O$, dimethyl ether, $CO_2$ and air.

The specialist will make the selection of these other substances according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of 0.0001 to 25 wt. % each, 0.0005 to 15 wt. %, based on the total weight of the respective agent.

Agent pH Value

The pH value of the agent as contemplated herein is preferably adjusted to a slightly acidic to alkaline pH value. Most preferably, the agent has an alkaline pH in the range of 4.0 to 11.5 preferably from 5.0 to 11.0.

To adjust the desired pH, the agent (a) and/or (b) may contain at least one alkalizing agent. The pH values for the purposes of the present disclosure are pH values measured at a temperature of 22° C.

As alkalizing agents, the agents may contain, for example, ammonia, alkanolamines and/or basic amino acids.

The alkanolamines which can be used in the agent of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment is therefore wherein the agent as contemplated herein comprises an alkanolamine selected from 2-aminoethan-1-ol and/or 2-amino-2-methylpropan-1-ol as alkalizing agent.

For the purposes of the present disclosure, an amino acid is an organic compound comprising at least one protonatable amino group and at least one —COOH or —$SO_3H$ group in its structure. Preferred amino acids are amino carboxylic acids, especially α-(alpha)-amino carboxylic acids and ω-amino carboxylic acids, whereby α-amino carboxylic acids are particularly preferred.

As contemplated herein, basic amino acids are those amino acids which have an isoelectric point pI of greater than 7.0.

Basic α-amino carboxylic acids contain at least one asymmetric carbon atom. In the context of the present disclosure, both enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In another particularly preferred embodiment, an agent as contemplated herein is therefore wherein the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In another very particularly preferred embodiment, a process as contemplated herein is wherein the colorant (a) comprises at least one alkalizing agent selected from the group of ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

To adjust the desired pH, the agent as contemplated herein may also contain at least one buffer system comprising at least one inorganic or organic acid and at least one salt of this acid.

A particularly well-suited inorganic acid is potassium dihydrogen phosphate. Potassium dihydrogen phosphate has the molecular formula $KH_2PO_4$ and carries the CAS number 7778-77-0. Potassium dihydrogen phosphate has a molar mass of 136.09 g/mol. It is highly soluble in water (222 g/l at 20° C.) and reacts acidically in water. A 5% solution of potassium dihydrogen phosphate in water has a pH value of 4.4.

Another particularly suitable inorganic acid (b2-I) is sodium dihydrogen phosphate. Sodium dihydrogen phosphate has the molecular formula $NaH_2PO_4$ and carries the CAS numbers 7558-80-7 (anhydrate), 10049-21-5 (monohdate) and 13472-35-0 (dihydrate). The anhydrous sodium dihydrogen phosphate has a molar mass of 119.98 g/mol. Sodium dihydrogen phosphate reacts acidically in aqueous solution.

Particularly preferred as a corresponding salt of the above two acids is dipotassium hydrogen phosphate. Dipotassium hydrogen phosphate has the molecular formula $K_2HPO_4$ and carries the CAS numbers 7758-11-4 (anhydrous) and 16788-57-1 (trihydrate). The anhydrous dipotassium hydrogen phosphate has a molar mass of 174.18 g/mol. Dipotassium hydrogen phosphate reacts alkaline in aqueous solution.

Also particularly preferred as a corresponding salt of the above two acids (b2-II) is disodium hydrogen phosphate. Disodium hydrogen phosphate has the molecular formula $Na_2HPO_4$ and carries the CAS numbers 7558-79-4 (anhydrous), 10028-24-7 (dihydrate), 7782-85-6 (heptahydrate) and 10039-32-4 (dodecahydrate). Anhydrous disodium hydrogen phosphate has a molar mass of 141.96 g/mol. Disodium hydrogen phosphate reacts alkaline in aqueous solution.

Process for Dyeing Keratin Material

The agents described above can be excellently used in processes for dyeing keratinous material, especially human hair.

A second object of the present disclosure is therefore a process for dyeing keratinous material, in particular human hair, in which an agent, as disclosed in detail in the description of the first object of the present disclosure, is applied to the keratinous fibers and, if necessary, rinsed out again after an exposure time of 30 seconds to 45 minutes.

In other words, a second object of the present disclosure is a process for coloring keratinous material, in particular human hair, comprising the following steps:
 (1) Application of a coloring agent to the keratinous material, wherein the coloring agent is an agent as disclosed in detail in the description of the first subject matter of the present disclosure,
 (2) Exposure of the colorant to the keratinous material and
 (3) Rinse out the dye with water.

In step (1) of the process as contemplated herein, the agent of the first present disclosure is applied to the keratinous material, which is most preferably human hair.

In step (2) of the process as contemplated herein, the agent is then allowed to act on the keratinous material after its application. In this context, different exposure times of, for example, 30 seconds to 60 minutes are conceivable.

However, a major advantage of the dyeing system as contemplated herein is that an intensive color result can be achieved even in short periods after short exposure times. For this reason, it is advantageous if the application mixture remains on the keratin material only for comparatively short periods of time after its application, from 30 seconds to 15 minutes, preferably from 30 seconds to 10 minutes, and particularly preferably from 1 to 5 minutes.

In a further preferred embodiment, a method as contemplated herein is.
exemplified by:
 (2) Exposure of the colorant to the keratinous material for a period ranging from 30 seconds to 15 minutes, preferably from 30 seconds to 10 minutes, and most preferably from 1 to 5 minutes.

Finally, following the action of the application mixture on the keratin material, it is rinsed with water in step (3) of the process.

Here, in one embodiment, the application mixture can be washed out with water only, i.e., without the aid of an after-treatment agent or a shampoo. The use of a post-treatment agent or conditioner in step (6) is also conceivable in principle.

However, to solve the task as contemplated herein and to increase the convenience of use, it has proved particularly preferable to rinse the agent in step (3) exclusively with water without the aid of a further after-treatment agent, shampoo, or conditioner.

In a further preferred embodiment, a method as contemplated herein is.
exemplified by:
 (3) Rinse out the dye with water only.

Process for Dyeing Keratin Material, in which the Agent Ready for Use is First Prepared.

As previously described, the agent of the first subject present disclosure is an application-ready agent that is either provided directly to the user in its application-ready form or is prepared by mixing various agents just prior to application.

To ensure a particularly fine distribution of the pigments, it has proved particularly preferable to prepare the ready-to-use agent shortly before application by mixing two or three different agents.

Accordingly, in a particularly preferred embodiment, the ready-to-use agent is prepared by mixing at least two different agents, the first of these two agents comprising the mixture of alkyl (poly)glycoside (a1) and pigment(s) (a2). For example, the mixture of alkyl (poly)glycoside (a1) and pigment(s) (a2) may represent a predispersion provided in the form of a concentrate. The second agent comprises at least one amino-functionalized silicone polymer (a3) and may, for example, be a water-comprising cosmetic carrier formulation. To prepare the ready-to-use agent, the two agents are then shaken or stirred together.

A further subject of the present application is therefore a process for coloring keratinous material, in particular human hair, comprising the following steps:
 (1) Providing an agent (I), wherein the agent (I) comprises:
  (a1) at least one alkyl(poly)glycoside and
  (a2) at least pigment,
 (2) Providing an agent (II), wherein the agent (II) comprises:
  (a3) at least one amino-functionalized silicone polymer.
 (3) Prepare an application mixture by mixing agents (I) and (II),
 (4) Apply the application mixture prepared in step (3) to the keratinous material,
 (5) exposure of the application mixture applied in step (4) to the keratinous material; and
 (6) Rinse the application mixture with water,
wherein the ingredients (a1), (a2) and (a3) have already been disclosed in detail in the description of the first subject matter of the present disclosure.

The agent (I) here preferably represents a predispersion of the pigments (a2) in the alkyl poly)glycoside(s) (a1), which may be in the form of a concentrate, for example.

The agent (II) is a base formulation, preferably in the form of a base cream, comprising the amino silicone(s) (a3). When agents (I) and (II) are mixed, the predispersion of the pigments (a2) in the $C_2$-$C_{30}$ alkyl methicone (a1) ensures a particularly fine distribution of the pigments, which is retained in the ready-to-use agent even after mixing of the two agents (I) and (II).

Depending on the selected pH, the amino silicone (a3) has in some cases shown reduced storage stability in aqueous environments. In these cases, it may be advantageous to also use the
amino functionalized silicone polymer (a3) in a separate agent and to mix both the predispersion (a1)/(a2) and the amino silicone (a3) with a base formulation only shortly before use. In this case, at least three different agents are mixed to produce the ready-to-use colorant.

Accordingly, a further subject matter is a process for coloring keratinous material, in particular human hair, comprising the following steps:
  (1) Providing an agent (I), wherein the agent (I) comprises:
    (a1) at least one alkyl(poly)glycoside and
    (a2) at least pigment,
  (2) Providing an agent (II), wherein the agent (II) is an aqueous cosmetic carrier formulation,
  (3) Providing an agent (III), wherein the agent (III) comprises:
    (a3) at least one amino-functionalized silicone polymer (a3),
  (4) Prepare an application mixture by mixing agents (I) and (II) and (III),
  (5) Apply the application mixture prepared in step (4) to the keratinous material,
  (6) exposure of the application mixture applied in step (5) to the keratinous material; and
  (7) Rinse the application mixture with water,
wherein the ingredients (a1), (a2) and (a3) have already been disclosed in detail in the description of the first subject matter of the present disclosure.

In the context of this embodiment, the agent (I) preferably represents a predispersion of the pigments (a2) in the alkyl (poly)glycoside(s) (a1), which may be in the form of a concentrate, for example. The agent (III) is preferably also a concentrate comprising the amino-functionalized silicone polymer(s) (a3).

Before application, the two agents or concentrates (I) and (III) are then mixed with the carrier formulation (II). The order of mixing is arbitrary. Thus, agents (I) and (II) can first be mixed with each other, whereupon this mixture is then mixed with agent (III). Likewise, it is conceivable to first mix agents (II) and (III) and then mix this mixture with agent (I). Also, all three agents (I), (II) and (III) can be added together and then mixed by shaking or stirring first.

The carrier formulation comprises water and preferably has a high-water content. The optionally applicable further ingredients of the first present disclosure may also be included in this carrier formulation.

Particularly preferred here is also the
  (2) Providing an agent (II), wherein the agent (II) is water-comprising and comprises at least one fatty component and/or at least one surfactant.

Finally, in a further embodiment, it may prove advantageous to also separate the components (a1) and (a2) from one another, so that the three components (a1), (a2) and (a3) previously separated from one another are mixed with the preparation of the agent ready for use. This form of production can be advantageous, for example, if the pigment or pigments (a2) are to be used in smaller quantities and/or in the form of a powder. Packaging the pigments in powder form simplifies the quantitative transfer of the pigments into a mixing vessel or other container.

A further object of the present application is thus a process for coloring keratinous material, in particular human hair, comprising the following steps:
  (1) Providing an agent (I), wherein the agent (I) comprises:
    (a1) at least one alkyl (poly)glycoside,
  (2) Providing an agent (II), wherein the agent (II) comprises:
    (a2) at least pigment,
  (3) Providing an agent (III), wherein the agent (III) comprises:
    (a3) at least one amino-functionalized silicone polymer,
  (4) Prepare an application mixture by mixing agents (I) and (II) and (III),
  (5) Apply the application mixture prepared in step (4) to the keratinous material,
  (6) exposure of the application mixture applied in step (5) to the keratinous material; and
  (7) Rinse the application mixture with water,
wherein the ingredients (a1), (a2) and (a3) have already been disclosed in detail in the description of the first subject matter of the present disclosure.

Here, the agent (I) comprises at least one alkyl (poly) glycoside (a1) and may be in the form of a concentrate, for example. It is also as contemplated herein if the agent (I) is in the form of a carrier formulation or a carrier cream which comprises—in addition to other optional ingredients—the surfactant (a1).

The agent (II) comprises at least one pigment (a2). In one form of packaging, the pigment is provided, for example, in the form of a powder.

The agent (III) comprises at least one amino-functionalized silicone polymer (a3) and is preferably in the form of a concentrate.

Multi-Component Packaging Unit

To increase user convenience, the agents described above can be provided to the user in the form of a multi-component packaging unit.

A further object is therefore a multi-component packaging unit (kit-of-parts) for dyeing keratinous material, in particular human hair, comprising separately prepared
  a first container comprising an agent (I), the agent (I) comprising:
    (a1) at least one alkyl(poly)glycoside and
    (a2) at least pigment,
  a second container comprising an agent (II), the agent (II) comprising:
    (a3) at least one amino-functionalized silicone polymer,
wherein the ingredients (a1), (a2) and (a3) have already been disclosed in detail in the description of the first subject matter of the present disclosure.

Another object of the present application is a multi-component packaging unit (kit-of-parts) for dyeing keraitnic material, in particular human hair, comprising separately prepared
  a first container comprising an agent (I), the agent (I) comprising:
    (a1) at least one alkyl (poly)glycoside,
  a second container comprising an agent (II), the agent (II) comprising:
    (a2) at least pigment,
  a third container comprising an agent (III); said agent (III) comprising:
    (a3) at least one amino-functionalized silicone polymer, wherein the ingredients (a1), (a2) and (a3) have already been disclosed in detail in the description of the first subject matter of the present disclosure.

Regarding the further preferred embodiments of the processes as contemplated herein and of the multi-component packaging unit as contemplated herein, mutatis mutandis what has been said about the agent as contemplated herein applies.

EXAMPLES

1. Formulations

The following formulations were prepared (all data in weight percent unless otherwise indicated):

| ready-to-use dye | V | E1 | E2 |
|---|---|---|---|
| Cetyl alcohol | 3.6 | 3.6 | 3.6 |
| Stearyl alcohol | 2.0 | 2.0 | 2.0 |
| Paraffinum Liquidum | 2.1 | 2.1 | 2.1 |
| Ceteareth-30 | 1.2 | 1.2 | 1.2 |
| Ceteareth-100 | 0.6 | 0.6 | 0.6 |
| Glyceryl stearate | 0.6 | 0.6 | 0.6 |
| Potassium dihydrogen phosphate | 0.35 | 0.35 | 0.35 |
| Disodium hydrogen phosphate | 0.72 | 0.72 | 0.72 |
| Phenoxyethanol | 0.9 | 0.9 | 0.9 |
| cc (CAS Number 110615-47-9) (a1) | — | 2.5 | 2.5 |
| Unipure Red LC 3071 (CI 15850, Sensient) (a2) | 0.5 | 0.5 | 0.5 |
| Amino silicone (Dow Corning 2-8566 (Siloxanes and Silicones, cc) (a3) | 1.0 | 1.0 | 1.0 |
| Water | ad 100 | ad 100 | ad 100 |

2. Preparation of the Agents Ready for Use and Application

First, a carrier formulation or base cream was prepared. For this purpose, cetyl alcohol, stearyl alcohol and paraffinum liquidum were mixed and heated to 80° C. with stirring. Then ceteareth-30, ceteareth-100 and glyceryl stearate were added with stirring. Water was used to make up to the appropriate amount in each case, then the phosphate salts and phenoxyethanol were added. Ingredients (a1), (a2) and (a3) were then added to this base cream as indicated in the table.

| V | E1 | E2 |
|---|---|---|
| 98.5 g base cream was submitted. With stirring, the cream was mixed with 0.5 g pigment (a2) and 1.0 g amino silicone (a3). | 96.0 g base cream was submitted. 0.5 g pigment (a2) was predispersed in 2.5 g lauryl glucoside (a1). With stirring, the cream was mixed with the predispersion and then with 1.0 g of amino silicone (a3). | 96.0 g of the base cream was submitted, 2.5 g of lauryl glucoside (a1) was incorporated into this cream. With stirring, the cream was then mixed with 0.5 g pigment (a2) and with 1.0 g amino silicone (a3). |

The ready-to-use agents obtained in this way were applied to a strand of hair (Kerling company, "Euronatur-hair white" (ENH) type) (liquor ratio: 1 g agent per g strand of hair) and left to act for three minutes. Subsequently, the hair strand was thoroughly (1 minute) washed with water and dried.

3. Measurement of Wash Fastness

After drying, the dyed strands were measured with a colorimeter from Datacolor, type Spectraflash 450.

After that, each strand was washed by hand three times. For this purpose, each strand was moistened with water, then a commercial shampoo (Schauma 7-herbs) was applied to the strand (0.25 g of shampoo per 1 g of hair) and massaged in with the fingers for 30 seconds. Then the strand was rinsed under lukewarm running water for 1 minute and the hair strand was dried. The previously described process corresponds to a hair wash. For each subsequent hair wash the procedure was repeated. After 3 hair washes, the strands were colorimetrically measured again.

The dE value used for the assessment of wash fastness is derived from the L*a*b* colorimetric values measured on the respective strand as follows:

$$dE=[(L_i-L_0)^2+(a_i-a_0)^2+(b_i-b_0)]^{1/2}$$

$L_0$, $a_0$ and $b_0$=Measured values directly after dyeing
$L_i$, $a_i$ and $b_i$=Measured values after 3 hair washes The smaller the dE value, the smaller the color difference compared to dyed, unwashed hair and the better the wash fastness.

| Wash fastness | | L | a | b | dE |
|---|---|---|---|---|---|
| V | directly after dyeing | 41.82 | 48.36 | 5.09 | 38.8 |
| | after 3 hair washes | 65.71 | 17.88 | 6.97 | |
| E1 | directly after dyeing | 52.94 | 33.99 | 4.39 | 21.9 |
| | after 3 hair washes | 66.43 | 17.33 | 9.00 | |
| E2 | directly after dyeing | 45.97 | 43.93 | 5.55 | 4.8 |
| | after 3 hair washes | 48.47 | 40.73 | 3.02 | |

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An agent for dyeing keratinous material, comprising:
(a1) at least one alkyl (poly)glucoside;
(a2) at least one pigment having a solubility of less than 0.5 g/L in water at 25° C.; and
(a3) at least one amino-functionalized silicone polymer;
wherein the agent comprises from 60.0 to 90.0 wt. % of water, based on the total weight of the agent.

2. The agent of claim 1,
wherein the at least one alkyl (poly)glucoside (a1) comprises an alkyl(poly)glucoside of the formula (APG-1):

$$(Z)_x—O—(CH_2)_n—CH_3 \qquad (APG-1),$$

where
each Z is a sugar component selected from glucose,
x is a number from 1 to 10, and
n is a number from 7 to 29.

3. The agent of claim 1, wherein the at least one alkyl (poly)glucoside (a1) comprises an alkyl (poly)glucoside of the formula (APG-2):

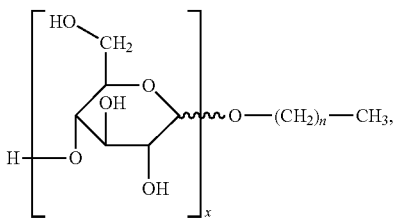
(APG-2)

where
x is a number from 1 to 10, and
n is a number from 7 to 29.

4. The agent of claim 1, comprising the one or more alkyl (poly)glucosides (a1) in a total amount of from about 0.1 to about 20.0 wt. %, based on the total weight of the agent.

5. The agent of claim 1, wherein the at least one pigment (a2) comprises at least one inorganic pigment selected from colored metal oxides, metal hydroxides, metal oxide hydrates, silicates, metal sulfides, complex metal cyanides, metal sulfates, bronze pigments, and mica- or mica-based colored pigments coated with at least one metal oxide and/or a metal oxychloride.

6. The agent of claim 1, wherein the at least one pigment (a2) comprises at least one organic pigment (a2) selected from carmine, quinacridone, phthalocyanine, Sorgho, blue pigments with the color index numbers CI 42090, CI 69800, CI 69825, CI 73000, CI 74100, CI 74160, yellow pigments with the color index numbers CI 11680, CI 11710, CI 15985, CI 19140, CI20040, CI21100, CI21108, CI47000, CI47005, green pigments with Color Index numbers CI 61565, CI 61570, CI 74260, orange pigments with Color Index numbers CI 11725, CI 15510, CI 45370, CI 71105, and/or red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

7. The agent of claim 1, comprising the at least one pigment (a2) in a total amount of from about 0.1 to about 10.0 wt. %, based on the total weight of the agent.

8. The agent of claim 1, wherein the at least one amino-functionalized silicone polymer (a3) comprises at least one secondary amino group.

9. The agent of claim 8, wherein the at least one amino-functionalized silicone polymer (a3) comprises at least one structural unit of the formula (Si-Amino):

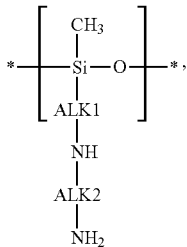
(Si-Amino)

where
each ALK1 and ALK2 independently represents a linear or branched $C_1$-$C_{20}$ divalent alkylene group.

10. The agent of claim 8, wherein the at least one amino-functionalized silicone polymer (a3) comprises structural units of the formula (Si-I) and structural units of the formula (Si-II):

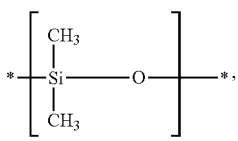
(Si-I)

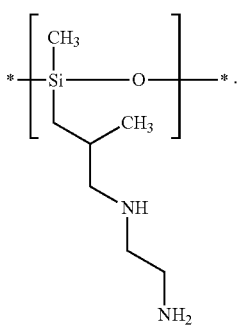
(Si-II)

11. The agent of claim 1, comprising the at least one amino-functionalized silicone polymer (a3) in a total amount of from about 0.1 to about 8.0 wt. %, based on the total weight of the agent.

12. A process for dyeing keratinous material, comprising:
applying the agent of claim 1 to keratinous fibers; and
optionally, rinsing the keratinous fibers to remove the agent after an exposure time of from about 30 seconds to about 45 minutes.

13. A process for dyeing keratinous material, comprising:
preparing an application mixture comprising the agent of claim 1 by mixing together
(I) a first agent comprising the at least one alkyl(poly)glucoside (a1) and the at least pigment (a2), and
(II) a second agent comprising the at least one amino-functionalized silicone polymer (a3);
applying the application mixture to keratinous material for a time sufficient to expose the keratinous material to the agent; and
rinsing the application mixture from the keratinous material with water.

14. The process of claim 13, wherein preparing the application further comprises mixing (III) a third agent with the first agent (I) and the second agent (II), the third agent comprising an aqueous cosmetic carrier formulation.

15. A process for dyeing keratinous material, comprising:
preparing an application mixture comprising the agent of claim 1 by mixing together
(I) a first agent comprising the at least one alkyl(poly)glucoside (a1),
(II) a second agent comprising the at least one pigment (a2), and
(III) a third agent comprising the at least one amino-functionalized silicone polymer (a3);
applying the application mixture to keratinous material for a time sufficient to expose the keratinous material to the agent; and
rinsing the application mixture from the keratinous material with water.

16. A multicomponent packaging unit (kit-of-parts) for dyeing keratinous material with the agent of claim 1, comprising, separately packaged:
   a first container comprising (I) a first agent comprising the at least one alkyl(poly)glucoside (a1) and the at least pigment (a2); and
   a second container comprising (II) a second agent comprising the at least one amino-functionalized silicone polymer (a3).

17. A multicomponent packaging unit (kit-of-parts) for dyeing keratinous material with the agent of claim 1, comprising, separately packaged:
   a first container comprising (I) a first agent comprising the at least one alkyl(poly)glucoside (a1);
   a second container comprising (II) a second agent comprising the at least pigment (a2); and
   a third container comprising (III) a third agent comprising the at least one amino-functionalized silicone polymer (a3).

18. The agent of claim 1, wherein:
   the at least one alkyl (poly)glucoside (a1) comprises an alkyl (poly)glucoside of the formula (APG-1):

$$(Z)_x\text{—O—}(CH_2)_n\text{—}CH_3 \qquad (APG\text{-}1),$$

where each Z is a sugar component selected from glucose, where x is a number from 1 to 5, and where n is a number from 7 to 21;
   the at least one pigment (a2) comprises at least one inorganic pigment and at least one organic pigment; and
   the at least one amino-functionalized silicone polymer (a3) comprises structural units of the formula (Si-I) and structural units of the formula (Si-II):

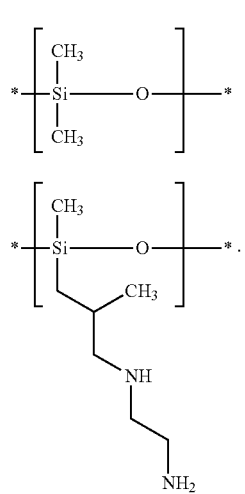

(Si-I)

(Si-II)

19. The agent of claim 18, comprising, each based on the total weight of the agent:
   a total amount of from about 2.0 to about 6.0 wt. % of the at least one alkyl (poly)glucoside (a1);
   a total amount of from about 0.25 to about 1.5 wt. % of the at least one pigment (a2); and
   a total amount of from about 0.4 to about 2.5 wt. % of the at least one amino-functionalized silicone polymer (a3); and
   a total amount of from 70.0 to 90.0 wt. % of water.

20. The agent of claim 1, wherein:
   the at least one alkyl (poly)glucoside (a1) consists essentially of lauryl glucoside, and is present in a total amount of from about 2.0 to about 6.0 wt. % based on the total weight of the agent;
   the at least one pigment (a2) consists essentially of an inorganic pigment selected from colored metal oxides, metal hydroxides, metal oxide hydrates, silicates, metal sulfides, complex metal cyanides, metal sulfates, bronze pigments and/or mica- or mica-based colored pigments coated with at least one metal oxide and/or a metal oxychloride, and is present in a total amount of from about 0.25 to about 1.5 wt. % based on the total weight of the agent; and
   the at least one amino-functionalized silicone polymer (a3) is present in a total amount of from about 0.4 to about 2.5 wt. % based on the total weight of the agent, and comprises an amino-functional silicone polymer having the formula (Si-III):

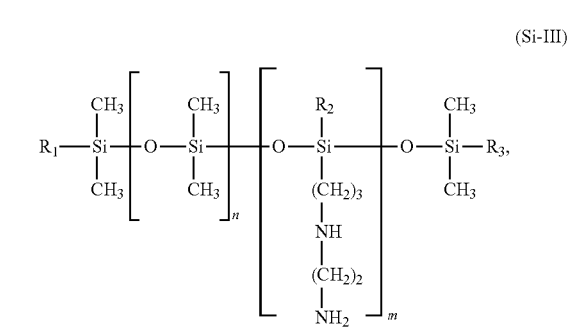

(Si-III)

where $R_1$, each $R_2$, and $R_3$ is independently selected from hydroxy groups and $C_1$-$C_4$ alkoxy groups, with the proviso that at least one of $R_1$, $R_2$, and $R_3$ is a hydroxy group, and where m is from 1 to 1000 and n is from 0 to 999, with the proviso that that sum of m+n is from 1 to 1000.

* * * * *

UNITED STATES PATENT AND TRADEMARK OFFICE
CERTIFICATE OF CORRECTION

PATENT NO. : 12,246,197 B2
APPLICATION NO. : 18/002466
DATED : March 11, 2025
INVENTOR(S) : Constanze Kruck et al.

Page 1 of 1

It is certified that error appears in the above-identified patent and that said Letters Patent is hereby corrected as shown below:

In the Specification

Column 17, Line 42 & 43 change "$(CH_3)_3$ SI-$[O-Si(CH_3)_2]_n[OSi(CH_3)]_m$-$OSi(CH_3)_3$" to --$(CH_3)_3$ Si-$[O-Si(CH_3)_2]_n[OSi(CH_3)]_m$-$OSi(CH_3)_3$--.

Column 30, Line 54 change "omithine" to --ornithine--.

Signed and Sealed this
Fifteenth Day of July, 2025

Coke Morgan Stewart
*Acting Director of the United States Patent and Trademark Office*